(12) United States Patent
Modha et al.

(10) Patent No.: US 10,925,335 B2
(45) Date of Patent: Feb. 23, 2021

(54) BREACH DETECTION GLOVE WITH A HIGH CONTRAST BETWEEN THE COLOR ON THE DONNING SIDE AND THE GRIP SIDE OF THE GLOVE

(71) Applicant: O&M Halyard, Inc., Mechanicsville, VA (US)

(72) Inventors: Shantilal H. Modha, Milton, GA (US); Patrick H. Robert, Alpharetta, GA (US); Sopha Issara, Songkhala (TH); Zamsari Zakaria, Perak (MY)

(73) Assignee: O&M Halyard, Inc., Mechanicsville, VA (US)

( * ) Notice: Subject to any disclaimer, the term of this patent is extended or adjusted under 35 U.S.C. 154(b) by 193 days.

(21) Appl. No.: 15/776,908

(22) PCT Filed: Nov. 18, 2016

(86) PCT No.: PCT/US2016/062765
§ 371 (c)(1),
(2) Date: May 17, 2018

(87) PCT Pub. No.: WO2017/087797
PCT Pub. Date: May 26, 2017

(65) Prior Publication Data
US 2018/0332910 A1 Nov. 22, 2018

Related U.S. Application Data

(60) Provisional application No. 62/257,276, filed on Nov. 19, 2015.

(51) Int. Cl.
*A41D 19/00* (2006.01)
*B32B 25/04* (2006.01)
(Continued)

(52) U.S. Cl.
CPC ..... *A41D 19/0082* (2013.01); *A41D 19/0006* (2013.01); *A61B 42/10* (2016.02);
(Continued)

(58) Field of Classification Search
CPC .......... B32B 2307/402; B32B 2437/02; B32B 25/042; B32B 25/08; B32B 27/40;
(Continued)

(56) References Cited

U.S. PATENT DOCUMENTS

| 4,888,829 A | 12/1989 | Kleinerman et al. |
| 5,650,225 A | 7/1997 | Dutta et al. |

(Continued)

FOREIGN PATENT DOCUMENTS

| CN | 1483058 A | 3/2004 |
| CN | 1631645 A | 6/2005 |

(Continued)

OTHER PUBLICATIONS

Cruse, Phil, "Introduction to the CIE LCH & Lab Colour Spaces", May 17, 2016, 4 pages.
(Continued)

*Primary Examiner* — Yan Lan
(74) *Attorney, Agent, or Firm* — Dority & Manning, P.A.

(57) ABSTRACT

Elastomeric articles, such as gloves, made from more than one layer, are provided. The gloves can include a first (grip side) layer in which a first colorant is compounded or integrated and a second (donning side) layer in which a second colorant is compounded or integrated. Alternatively, the gloves can include a translucent first layer and a second layer in which a colorant is compounded or integrated. Either arrangement can enable a breach of the first layer to be more easily detected, either due to the high level of contrast between the first layer and the second when a first colorant and a second colorant are utilized, or due to the (Continued)

translucence of the first layer as compared to the donning side layer, where the intensity of the second layer is increased upon a breach of the translucent first layer.

13 Claims, 7 Drawing Sheets

(51) Int. Cl.
| | |
|---|---|
| B32B 25/08 | (2006.01) |
| B32B 27/40 | (2006.01) |
| B29C 41/00 | (2006.01) |
| B29C 41/22 | (2006.01) |
| B29C 41/14 | (2006.01) |
| A61B 42/30 | (2016.01) |
| A61B 42/10 | (2016.01) |
| B29L 31/48 | (2006.01) |
| B29K 105/00 | (2006.01) |
| B29L 9/00 | (2006.01) |
| B29K 19/00 | (2006.01) |
| B29K 75/00 | (2006.01) |

(52) U.S. Cl.
CPC ............ *A61B 42/30* (2016.02); *B29C 41/003* (2013.01); *B29C 41/14* (2013.01); *B29C 41/22* (2013.01); *B32B 25/042* (2013.01); *B32B 25/08* (2013.01); *B32B 27/40* (2013.01); *A41D 2400/44* (2013.01); *B29K 2019/00* (2013.01); *B29K 2075/00* (2013.01); *B29K 2105/0032* (2013.01); *B29L 2009/00* (2013.01); *B29L 2031/4864* (2013.01); *B32B 2307/402* (2013.01); *B32B 2437/02* (2013.01)

(58) Field of Classification Search
CPC ......... B29L 2009/00; B29L 2031/4864; B29K 2019/00; B29K 2075/00; B29K 2105/0032; B29C 41/003; B29C 41/14; B29C 41/22; A61B 42/10; A61B 42/30; A41D 19/0006; A41D 19/0082; A41D 2400/44
See application file for complete search history.

(56) References Cited

U.S. PATENT DOCUMENTS

| | | | |
|---|---|---|---|
| 6,973,675 B2 * | 12/2005 | Cheng | A41D 19/0058 2/161.7 |
| 7,183,347 B2 | 2/2007 | Ota et al. | |
| 7,378,043 B2 | 5/2008 | Hassan et al. | |
| 7,585,526 B2 | 9/2009 | Hamann | |
| 7,923,498 B2 | 4/2011 | Foo | |
| 8,117,672 B2 | 2/2012 | Lipinski | |
| 2003/0124354 A1 | 7/2003 | Vistins | |
| 2006/0026737 A1 | 2/2006 | Chen | |
| 2006/0150300 A1 | 7/2006 | Hassan et al. | |
| 2006/0253956 A1 * | 11/2006 | Lipinski | C08L 9/02 2/168 |
| 2007/0104904 A1 * | 5/2007 | Hamann | B32B 25/042 428/35.7 |
| 2008/0311409 A1 | 12/2008 | Lipinski | |
| 2009/0070918 A1 | 3/2009 | Pickard et al. | |
| 2009/0143516 A1 | 6/2009 | MacDonald et al. | |
| 2013/0104286 A1 * | 5/2013 | Shawver | A61B 42/00 2/168 |
| 2018/0312671 A1 * | 11/2018 | Inthasaro | C08L 9/02 |

FOREIGN PATENT DOCUMENTS

| | | |
|---|---|---|
| CN | 101175809 A | 5/2008 |
| CN | 101268135 A | 9/2008 |
| EP | 1 361 247 A1 | 11/2003 |
| JP | 2015-025160 A | 2/2014 |
| RU | 2545541 C2 | 4/2015 |
| WO | WO 2006/075980 A1 | 7/2006 |
| WO | WO 2007/011309 A1 | 1/2007 |

OTHER PUBLICATIONS

Konica Minolta Sensing Americas. Inc., "Colorimetry—How to Measure Color Differences", Photonics Handbook, Oct. 6, 2015, 3 pages.
International Search Report and Written Opinion for PCT/US2016/062765, dated Apr. 12, 2017, 14 pages.

* cited by examiner

BREACH DETECTION GLOVE WITH A HIGH CONTRAST BETWEEN THE COLOR ON THE DONNING SIDE AND THE GRIP SIDE OF THE GLOVE

RELATED APPLICATION

The present invention is the national stage entry of International Patent Application No. PCT/US2016/062765 having a filing date of Nov. 18, 2016, which claims priority to U.S. Provisional Application Ser. No. 62/257,276, filed on Nov. 19, 2015, both of which are incorporated herein in their entirety by reference thereto.

FIELD OF THE INVENTION

The present invention relates to elastomeric articles that are made from more than one layer of material. In particular, the invention pertains to any elastomeric glove (e.g., surgical, exam, industrial, emergency responder, etc.) containing at least two separate layers of elastomeric materials.

BACKGROUND OF THE INVENTION

The development of modern rubber materials has made possible the manufacture of a wide range of elastomeric articles, such as gloves, having varying properties of strength and chemical resistance. Gloves are used as an infection protection device to protect the wearer from exposure to bacteria, viruses, pathogens, infections, diseases, etc. that could transfer from a surface or bodily fluid (e.g., blood) to the wearer's skin. Gloves are also used in manufacturing environments to prevent the wearer from coming into contact with various chemicals, and in some medical settings, gloves can be used to protect the wearer from certain pharmaceuticals that may be toxic, such as chemotherapy drugs. Whether being used in a medical or manufacturing setting, there is a risk that the gloves could become punctured during use, such as when the gloves are used around sharps such as needles, scissors, blades, hemostats, etc. or equipment used in manufacturing. When such a puncture occurs, the protective barrier provided by the gloves is breached, and the wearer has an increased risk of exposure to bacteria, viruses, pathogens, infections, diseases, etc. It is important that the wearer be made aware of a breach of the protective barrier provided by the gloves, but in most instances, the breach is small (e.g., a puncture, hole, or tear from a small gauge needle), and the wearer may not notice that a breach has occurred. Further, depending on the environment in which the glove is being used, other factors may make the breach difficult to see. For example, the lighting may be poor, or the glove may be soiled or otherwise altered in appearance, making a small puncture nearly impossible to see. Moreover, while two-layered gloves have been available for use, one of the two layers is white, which is accomplished by simply adding titanium dioxide to one of the layers. However, it has not been feasible to form a colored layer where the color is even, uniform, and not muddied with pigment while at the same time achieving suitable saturation and value without a "bleed out" effect unless the other layer is white. In addition, because one of the layers is white, breach detection is difficult, particularly in industrial and manufacturing settings, where the wearer of the glove may come in contact with many hazardous materials. Thus, the wearer might not be aware or alerted to the fact that the glove has been breached upon seeing a whitish color present on the glove. Further, the environment surrounding the wearer may include walls, countertops, equipment, lighting, etc. that are white in color or that accentuate a white color, making it difficult for the wearer to discern a visual cue on a white glove.

As such, a need exists for a glove that enables quick identification of punctures, holes, tears, etc. so that the wearer notices immediately that his or her glove has been breached and that he or she is now exposed to the outside environment. Such a glove would allow the wearer to quickly change to a new pair of gloves to minimize his or her risk to exposure to the outside environment.

SUMMARY OF THE INVENTION

In accordance with one embodiment of the present invention, a multilayered elastomeric article is contemplated. The elastomeric article includes a first layer, wherein the first layer includes a first elastomeric material compounded with a first colored pigment; and a second layer, wherein the second layer includes a second elastomeric material compounded with a second colored pigment, wherein a sufficient level of contrast exists between the first layer and the second layer to detect a breach of the first layer.

In one particular embodiment, the first elastomeric material can include polyurethane, nitrile rubber, styrene-butadiene rubber, isobutylene-isoprene rubber, polychloroprene, polyisoprene, natural rubber, or a combination thereof, and the second elastomeric material can include polyurethane, nitrile rubber, styrene-butadiene rubber, isobutylene-isoprene rubber, polychloroprene, polyisoprene, natural rubber, or a combination thereof. In one embodiment, the first elastomeric material and the second elastomeric material can each include nitrile rubber. Further, the nitrile rubber can be compounded with an alkali agent, a metal oxide, a sulfur crosslinking agent, and a vulcanization accelerator. In another embodiment, the first elastomeric material can include polyurethane and the second elastomeric material can include nitrile rubber.

In another embodiment, the elastomeric article can be a glove, where the first layer defines a grip side layer of the glove and the second layer defines a donning side layer of the glove. However, it is also to be understood that the first layer can define a donning side layer of the glove and the second layer can define a grip side layer of the glove. The glove can include a cuff, where the cuff is formed from the second layer. In addition, the glove can have a palm region thickness ranging from about 0.01 millimeters to about 6 millimeters.

In still another embodiment, the first layer of the article can be darker than the second layer, where the first layer and the second layer exhibit a $\Delta E^*$ color difference greater than about 2.5 as determined according to the Commission Internationale de l'Eclairage (CIE) 1976 standard.

In an additional embodiment, the first colored pigment can be present in the first layer in an amount ranging from about 0.25 parts to about 5 parts based on 100 dry parts of the first elastomeric material.

In one more embodiment, the second colored pigment can be present in the second layer in an amount ranging from about 0.5 parts to about 15 parts based on 100 dry parts of the second elastomeric material.

In yet another embodiment, the second layer can include titanium dioxide, where the titanium dioxide is present in the second layer in an amount ranging from about 0.25 parts to about 30 parts based on 100 dry parts of the second elastomeric material. Further, the ratio of the parts of titanium dioxide to the parts of the colored pigment can range from about 0.25 to about 3. Moreover, the second layer can exhibit a saturation level of greater than about 25% and can exhibit a value level of greater than about 25%.

In another embodiment, a mask can be applied to form a graphic, pattern, logo, design, or text on the first layer, wherein the second layer is visible where the mask is applied.

In an additional embodiment, a breach of the first layer can expose the second colored pigment of the second layer to facilitate detection of the breach.

In yet another embodiment, the elastomeric article is reversible.

In accordance with another embodiment of the present invention, a multilayered elastomeric article is contemplated. The article includes a first layer, wherein the first layer is translucent and includes a first elastomeric material; and a second layer, wherein the second layer includes a second elastomeric material compounded with a colored pigment, wherein a sufficient level of contrast exists between the first layer and the second layer to detect a breach of the first layer.

In one particular embodiment, the first elastomeric material can include polyurethane, nitrile rubber, styrene-butadiene rubber, isobutylene-isoprene rubber, polychloroprene, polyisoprene, natural rubber, or a combination thereof, and the second elastomeric material can include polyurethane, nitrile rubber, styrene-butadiene rubber, isobutylene-isoprene rubber, polychloroprene, polyisoprene, natural rubber, or a combination thereof. In one embodiment, the first elastomeric material and the second elastomeric material can each include nitrile rubber. Further, the nitrile rubber can be compounded with an alkali agent, a metal oxide, a sulfur crosslinking agent, and a vulcanization accelerator. In another embodiment, the first elastomeric material can include polyurethane and the second elastomeric material can include nitrile rubber.

In another embodiment, the elastomeric article can be a glove, where the first layer defines a grip side layer of the glove and the second layer defines a donning side layer of the glove. However, it is also to be understood that the first layer can define a donning side layer of the glove and the second layer can define a grip side layer of the glove. The glove can include a cuff, wherein the cuff is formed from the second layer. In addition, the glove can have a palm region thickness ranging from about 0.01 millimeters to about 6 millimeters.

In an additional embodiment, the colored pigment can be present in the second layer in an amount ranging from about 0.5 parts to about 15 parts based on 100 dry parts of the second elastomeric material.

In one more embodiment, the second layer can include titanium dioxide, where the titanium dioxide is present in the second layer in an amount ranging from about 0.25 parts to about 30 parts based on 100 dry parts of the second elastomeric material. Further, the ratio of the parts of titanium dioxide to the parts of the colored pigment can range from about 0.25 to about 3. Moreover, the second layer can exhibit a saturation level of greater than about 25% and can exhibit a value level of greater than about 25%.

In yet another embodiment, a mask can be applied to form a graphic, pattern, logo, design, or text on the first layer, where the second layer is visible where the mask is applied.

In an additional embodiment, a breach of the first layer can expose the second colored pigment of the second layer to facilitate detection of the breach.

In yet another embodiment, the elastomeric article is reversible.

In accordance with an additional embodiment of the present invention, a method of making a multilayered elastomeric article is contemplated. The method includes: a) dipping a mold into a first solution comprising a first powder free coagulant, where the first powder free coagulant includes a first metallic salt, wherein the first metallic salt is present in an amount ranging from about 6 wt. % to about 14 wt. % based on the total wt. % of the first solution; b) dipping the mold into a first elastomeric formulation comprising a first elastomeric material to form a first layer; c) dipping the mold into a second solution comprising a second powder free coagulant, wherein the second powder free coagulant includes a second metallic salt, wherein the second metallic salt is present in an amount ranging from about 3 wt. % to about 22 wt. % based on the total wt. % of the second solution; d) dipping the mold into a second elastomeric formulation comprising a second elastomeric material to form a second layer; and e) curing the first elastomeric formulation and the second elastomeric formulation to form the multilayered elastomeric article, wherein a sufficient level of contrast exists between the first layer and the second layer to detect a breach of the first layer. Further, in some embodiments, a dip time for the second elastomeric formulation can be about 10% to about 90% shorter than a dip time for the first elastomeric formulation.

In one embodiment, the first metallic salt in the first solution and the second metallic salt in the second solution can include nitrate, sulfate, or chloride salts of calcium, aluminum, or zinc, or a combination thereof.

In an additional embodiment, the first solution, the second solution, or both can further comprise a wax, a hydrogel, a silicone, a gel, an inorganic powder, an antimicrobial agent, an acrylic polymer, a peroxide crosslinking agent, an emollient, a hydrophilic agent, a hydrophobic agent, a pigment, a colorant, a dye, a polyolefin-based powder, a surfactant, a soap, an acidic agent, an alkali agent, or a combination thereof.

In another embodiment, the first elastomeric material can include polyurethane, nitrile rubber, styrene-butadiene rubber, isobutylene-isoprene rubber, polychloroprene, polyisoprene, natural rubber, or a combination thereof, and the second elastomeric material can include polyurethane, nitrile rubber, styrene-butadiene rubber, isobutylene-isoprene rubber, polychloroprene, polyisoprene, natural rubber, or a combination thereof. In one embodiment, the first elastomeric material and the second elastomeric material can each include nitrile rubber. Further, the nitrile rubber in the first elastomeric material, the second elastomeric material, or both can be compounded with an alkali agent, a metal oxide, a sulfur crosslinking agent, and a vulcanization accelerator. In one particular embodiment, the first elastomeric material can include polyurethane, and the second elastomeric can include nitrile rubber.

In still another embodiment, the elastomeric article can be a glove, where the first layer forms a grip side layer of the glove and the second layer forms a donning side layer of the glove. The glove can include a cuff, where the cuff is formed from the second elastomeric formulation by dipping the mold farther into the second elastomeric formulation than the first elastomeric formulation. In addition, the glove can have a palm region thickness ranging from about 0.01 millimeters to about 6 millimeters.

In an additional embodiment, a first colored pigment can be compounded into the first layer in an amount ranging from about 0.25 parts to about 5 parts based on 100 dry parts of the first elastomeric material, and a second colored pigment can be compounded into the second layer in an amount ranging from about 0.5 parts to about 15 parts based on 100 dry parts of the second elastomeric material, further where titanium dioxide can be compounded into the second layer, where the titanium dioxide is present in the second layer in an amount ranging from about 0.25 parts to about 30 parts based on 100 dry parts of the second elastomeric material. Further, the ratio of the parts of titanium dioxide to the parts of the colored pigment can range from about 0.25 to about 3. Moreover, the second layer can exhibit a saturation level of greater than about 25% and can exhibit a value level of greater than about 25%.

In one more embodiment, the first layer can be darker than the second layer, where the first layer and the second layer exhibit a $\Delta E^*$ color difference greater than about 2.5 as determined according to the Commission Internationale de l'Eclairage (CIE) 1976 standard.

In still another embodiment, the first layer can be translucent, where a colored pigment is compounded into the second layer in an amount ranging from about 0.5 parts to about 15 parts based on 100 dry parts of the second elastomeric material, and further where titanium dioxide can be compounded into the second layer, where the titanium dioxide is present in the second layer in an amount ranging from about 0.25 parts to about 30 parts based on 100 dry parts of the second elastomeric material. Further, the ratio of the parts of titanium dioxide to the parts of the colored pigment can range from about 0.25 to about 3. Moreover, the second layer can exhibit a saturation level of greater than about 25% and can exhibit a value level of greater than about 25%.

In another embodiment, a mask can be applied to form a graphic, pattern, logo, design, or text on the first layer, wherein the second layer is visible where the mask is applied.

In one more embodiment, a breach of the first layer exposes the second layer to facilitate detection of the breach by a user.

In accordance with one more embodiment of the present invention, a method of making a multilayered elastomeric article is contemplated. The method includes: a) dipping a mold into a solution comprising a powder free coagulant, wherein the powder free coagulant includes a metallic salt, wherein the metallic salt is present in an amount ranging from about 3 wt. % to about 22 wt. % based on the total wt. % of the solution; b) dipping the mold into a first elastomeric formulation comprising a first elastomeric material to form a first layer; c) dipping the mold into a second elastomeric formulation comprising a second elastomeric material to form a second layer; and d) curing the first elastomeric formulation and the second elastomeric formulation to form the multilayered elastomeric article, wherein a sufficient level of contrast exists between the first layer and the second layer to detect a breach of the first layer. Further, in some embodiments, a dip time for the second elastomeric formulation can be about 40% to about 100% longer than a dip time for the first elastomeric formulation.

In one embodiment, the metallic salt can include nitrate, sulfate, or chloride salts of calcium, aluminum, or zinc, or a combination thereof.

In an additional embodiment, the solution can further comprise a wax, a hydrogel, a silicone, a gel, an inorganic powder, an antimicrobial agent, an acrylic polymer, a peroxide crosslinking agent, an emollient, a hydrophilic agent, a hydrophobic agent, a pigment, a colorant, a dye, a polyolefin-based powder, a surfactant, a soap, an acidic agent, an alkali agent, or a combination thereof.

In another embodiment, the first elastomeric material can include polyurethane, nitrile rubber, styrene-butadiene rubber, isobutylene-isoprene rubber, polychloroprene, polyisoprene, natural rubber, or a combination thereof, and the second elastomeric material can include polyurethane formulation, nitrile rubber, styrene-butadiene rubber, isobutylene-isoprene rubber, polychloroprene, polyisoprene, natural rubber, or a combination thereof. In one embodiment, the first elastomeric material and the second elastomeric material can each include nitrile rubber. Further, the nitrile rubber in the first elastomeric material, the second elastomeric material, or both can be compounded with an alkali agent, a metal oxide, a sulfur crosslinking agent, and a vulcanization accelerator. In yet another embodiment, the first elastomeric material can include polyurethane, and the second elastomeric can include nitrile rubber.

In an additional embodiment, the elastomeric article can be a glove, where the first layer forms a grip side layer of the glove and the second layer forms a donning side layer of the glove. The glove can include a cuff, where the cuff is formed from the second elastomeric formulation by dipping the mold farther into the second elastomeric formulation than the first elastomeric formulation. Further, the glove can have a palm region thickness ranging from about 0.01 millimeters to about 6.0 millimeters.

In one more embodiment, a first colored pigment can be compounded into the first layer in an amount ranging from about 0.25 parts to about 5 parts based on 100 dry parts of the first elastomeric material. In addition, a second colored pigment can be compounded into the second layer in an amount ranging from about 0.5 parts to about 15 parts based on 100 dry parts of the second elastomeric material. Moreover, titanium dioxide can be compounded into the second layer, where the titanium dioxide is present in the second layer in an amount ranging from about 0.25 parts to about 30 parts based on 100 dry parts of the second elastomeric material. Further, the ratio of the parts of titanium dioxide to the parts of the colored pigment can range from about 0.25 to about 3. Moreover, the second layer can exhibit a saturation level of greater than about 25% and can exhibit a value level of greater than about 25%.

In still another embodiment, the first layer can be darker than the second layer, where the first layer and the second layer exhibit a $\Delta E^*$ color difference greater than about 2.5 as determined according to the Commission Internationale de l'Eclairage (CIE) 1976 standard.

In one embodiment, the first layer can be translucent, where a colored pigment is compounded into the second layer in an amount ranging from about 0.5 parts to about 15 parts based on 100 dry parts of the second elastomeric material.

In addition, titanium dioxide can be compounded into the second layer, where the titanium dioxide is present in the second layer in an amount ranging from about 0.25 parts to about 30 parts based on 100 dry parts of the second elastomeric material. Further, the ratio of the parts of titanium dioxide to the parts of the colored pigment can range from about 0.25 to about 3. Moreover, the second layer can exhibit a saturation level of greater than about 25% and can exhibit a value level of greater than about 25%.

In an additional embodiment, a mask can be applied to form any desired graphic, pattern, logo, design, or text on the first layer, where the second layer is visible where the mask is applied.

In still another embodiment, a breach of the first layer can expose the second layer to facilitate detection of the breach by a user.

In one more embodiment, the method can include re-dipping the mold into the second elastomeric formulation comprising the second elastomeric material or dipping the mold into a third elastomeric formulation comprising a third elastomeric material prior to the curing step d.

Additional features and advantageous of the present invention will be revealed in the following detailed description. Both the foregoing summary and the following detailed description and examples are merely representative of the invention, and are intended to provide an overview for understanding the invention as claimed.

BRIEF DESCRIPTION OF THE FIGURES

A full and enabling disclosure of the present invention to one skilled in the art, including the best mode thereof, is set forth more particularly in the remainder of the specification, including reference to the accompanying figures, in which.

DETAILED DESCRIPTION OF REPRESENTATIVE EMBODIMENTS

Figure 1A:
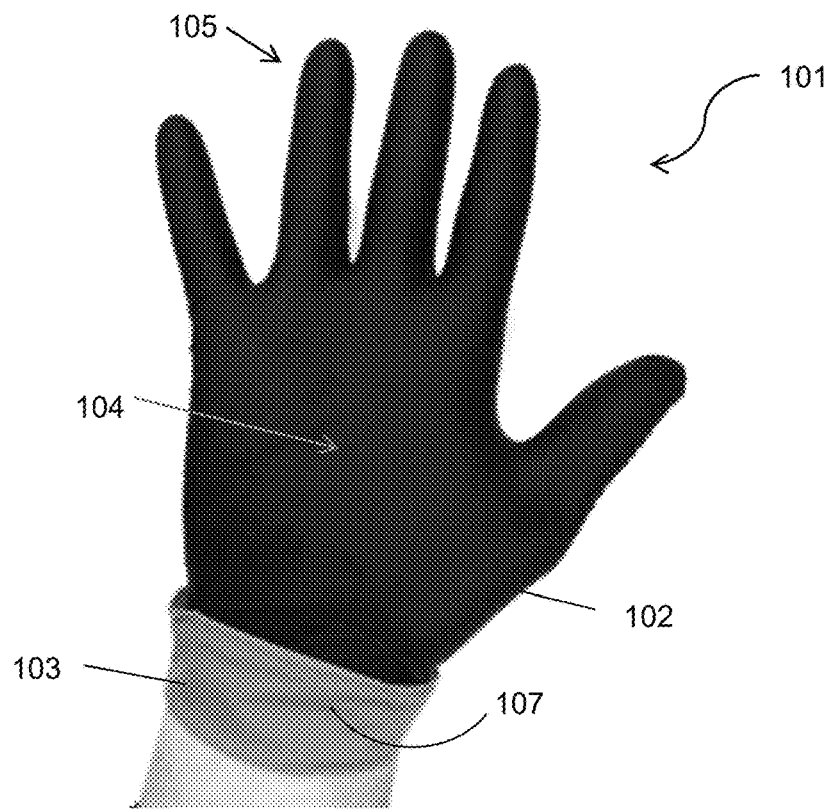
FIG. 1A illustrates one embodiment of the multilayered glove contemplated by the present invention, where a cuff has been formed by folding of the multilayered glove so that the donning side layer forms the outer layer of the cuff in order to illustrate the color contrast of the glove.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention describes the creation of elastomeric articles, such as gloves, made from more than one layer. In one embodiment, the glove can include a grip side layer in which a first colorant is compounded or integrated and a donning side layer in which a second colorant is compounded or integrated. Alternatively, in another embodiment, the glove can include a translucent grip side layer and a donning side layer in which a colorant is compounded or integrated, where the term translucent means allowing the passage of light, but not allowing objects beyond to be clearly seen while allowing contrasts to be seen. Either arrangement can enable a breach of the grip side layer to be more easily detected, either due to the high level of contrast between the grip side layer and the donning side layer when a first colorant and a second colorant are utilized, or due to the translucence of the grip side layer as compared to the donning side layer, where the intensity of the donning side layer is increased upon a breach of the translucent grip side layer.

In some embodiments, the layers can be separate layers that are not bonded to each other. Such a feature can be enabled by the use of materials that do not adhere to each other (e.g., nitrile and polyurethane) and/or through the use of a coagulant solution during the glove dipping process that can include an anti-tack agent. Moreover, because the two layers are not bonded to each other, the grip side layer can be removed during use if desired. For example, when used by an emergency responder, the grip side layer of the glove can be a darker color (e.g., black, brown, dark gray, blue, purple, etc.) and can be worn during the initial response to treat a patient. Then, once the patient is stabilized or when additional responders have arrived, the emergency responder can remove the grip side layer so that only the donning side layer is worn. The donning side layer can be a brighter color (e.g., green, orange, yellow, red, etc.) that can be more visible to bystanders for when the emergency responder directs traffic flow around an emergency scene. In addition, the glove can be reversible so that the brighter, donning side layer can be the grip side layer, such as in situations when enhanced visibility is desired (e.g., directing traffic, etc.). Referring to Table 1 below, in some embodiments, the grip side layer of the glove and the donning side layer of the glove can include the following color combinations, where possible Pantone color codes that can be used for the colorants are included in parentheses:

TABLE 1

| Glove Layer Color Combinations | |
|---|---|
| Grip Side | Donning Side |
| Black | Orange (2018U) |
| Black | Green (2286U) |
| Black | Blue (2174U) |
| Black | Red (2028U) |
| Black | Yellow (102U) |
| Black | Pink (238U) |
| Orange (2018U) | Black |
| Green (2286U) | Black |
| Blue (2174U) | Black |
| Red (2028U) | Black |
| Yellow (102U) | Black |
| Pink (238U) | Black |
| Grey (435U) | Purple (265U) |
| Grey (435U) | Orange (2018U) |
| Grey (435U) | Green (2286U) |
| Grey (435U) | Red (2028U) |

TABLE 1-continued

Glove Layer Color Combinations

| Grip Side | Donning Side |
| --- | --- |
| Grey (435U) | Blue (2174U) |
| Grey (435U) | Yellow (102U) |
| Dark Blue (2965U) | Green (2286U) |
| Dark Blue (2965U) | Yellow (102U) |
| Dark Blue (2965U) | Orange (2018U) |
| Green (2286U) | Purple (265U) |
| Purple (265U) | Green (2286U) |
| Purple (265U) | Yellow (102U) |
| Blue (2174U) | Yellow (102U) |
| Blue (2174U) | Orange (2018U) |
| Green (2286U) | Grey (435U) |
| Brown (4645U) | Dark Green (7743U) |
| Grey (435U) | Dark Blue (2965U) |

Figure 1B:
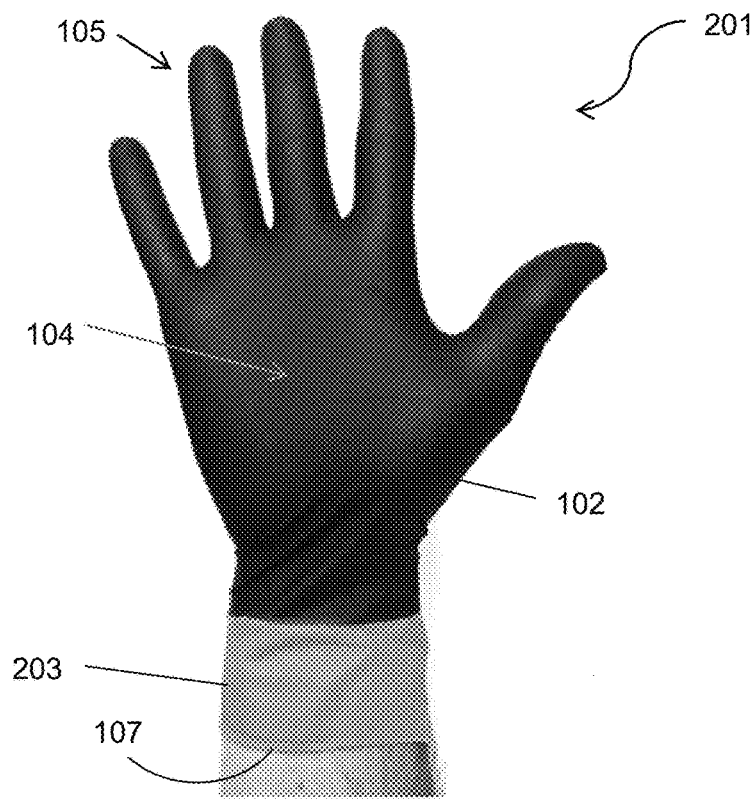
FIG. 1B illustrates another embodiment of the multilayered glove contemplated by the present invention, with a cuff formed by dipping a glove mold farther into the donning side layer formulation as compared to the grip side formulation.
Figure 2:
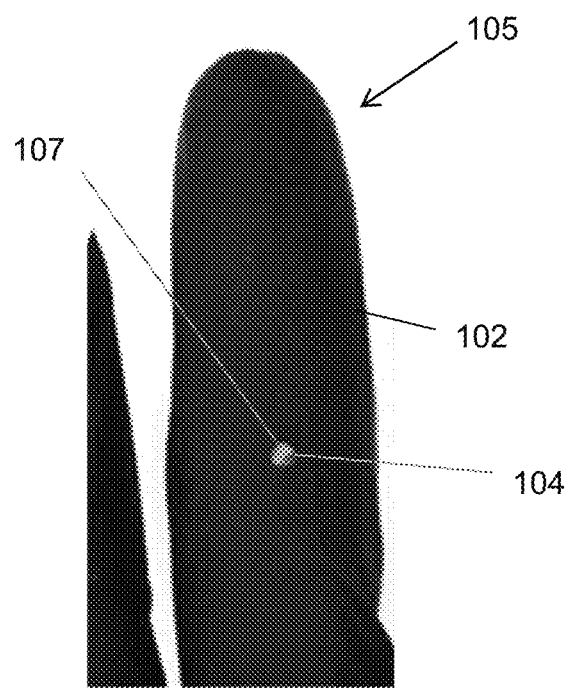
FIG. 2 illustrates the high contrast between the grip side and donning side of the glove of FIGS. 1A and 1B to facilitate the detection of a breach.

As shown in FIGS. 1A and 2, the elastomeric glove 101 has a finger region 105 and a palm region 106 and can include two layers that have a high color contrast or intensity difference in order to facilitate breach detection. In other words, a grip side layer 102 and a donning side layer 107 can have a sufficient level of color contrast so that a breach 104 of the outer layer or grip side layer 102 of the glove 101 can be easily detected since the donning side layer 107 can be visible through the breach (e.g., puncture or tear) 104 of the grip side layer 102. In the glove 101 of FIG. 1A, the grip side layer 102 and the donning side layer 107 of the glove have the same dimensions (e.g., the two layers are formed by dipping a glove mold into a donning side formulation and then into a grip side formulation at the same depth), after which the donning side layer 107 can optionally be folded over on its end to form a cuff 103 so that the color contrast between the two layers is visible. Further, it is to be understood that the glove 101 can be made in a manner such that the portion of the glove used to form the folded-over cuff 103 has an increased length to facilitate the ability for the wearer to fold the glove to form the cuff 103. In addition, in another embodiment, as shown in FIG. 1B, the donning side layer 107 can extend beyond the grip side layer 102 past the palm region 104 of glove 201 (e.g., the two layers are formed by dipping a glove mold into a donning side formulation and then into a grip side formulation, where the mold is dipped into the grip side formulation at a greater depth) to form a cuff 103 to provide the wearer with a cue as to the color contrast between the two layers.

In this regard, the term "contrast" means differences in appearance that are visually distinct to the naked eye, such as color differences, hue or value differences, tint or color saturation differences, opacity differences, translucence differences, and the differences related to the ability to see through articles. For instance, differences between similar colors can amount to a contrast if they demonstrate a color difference or distance between two colors, referred to by the Commission Internationale de l'Eclairage (CIE) as the ΔE* value, greater than about 2.3, where it is generally known that a ΔE* of 2.3 corresponds with a just noticeable color difference. Specifically, the color difference between the grip side layer and the donning side layer, in terms of the ΔE* value, can be greater than about 2.5, such as greater than about 3, such as greater than about 3.5, where the L*a*b* color value measurements, which refer to a sample's luminosity value (L*), red to green color difference value (a*), and yellow to blue color difference value (b*), and ΔE* calculations (CIE 1976 Commission Internationale de l'Eclairage) may be made using an X-Rite 938 Spectrodensitometer D65/10° using CMY filters, in accordance with the operator's manual, or any other suitable device. The X-Rite Spectrodensitometer may be obtained from the X-Rite Corporation of Grandville, Mich. Average optical densities are generally taken as the sum of the average of three measurements using each filter ΔE* is calculated in accordance with the following equation:

$$\Delta E^* = \text{SQRT}[(L^*\text{standard} - L^*\text{sample})^2 + (a^*\text{standard} - a^*\text{sample})^2 + (b^*\text{standard} - b^*\text{sample})^2]$$

Where L* represents lightness (0=black and 100=white). Further, the color channels, a* and b* will represent true neutral gray values at a*=0 and b*=0. The red/green opponent colors are represented along the a* axis, with green at negative a* values and red at positive a* values. Meanwhile, the yellow/blue opponent colors are represented along the b* axis, with blue at negative b* values and yellow at positive b* values. The higher the ΔE* value, the greater the change in color intensity. Testing may be conducted in accordance with ASTM DM 224-93; ASTM D2244-15a; and/or ASTM E308-90, or any other suitable method known by one of ordinary skill in the art. A detailed description of spectrodensitometer testing is available in *Color Technology in the Textile Industry*, 2nd Edition, Published 1997 by AATCC (American Association of Textile Chemists & Colorists).

The CIE L*c*h* color model can also be used to analyze the difference between two colors. Essentially it is in the form of a sphere. There are three axes; L*, c* and h°. The L* axis represents Lightness and is the vertical axis. L values can range from 0 at the bottom, which represents no lightness (i.e. absolute black) through 50 in the middle, to 100 at the top, which represents maximum lightness (i.e. absolute white). The c* axis represents chroma or saturation. This ranges from 0 at the center of the circle, which represents color that is completely unsaturated (i.e., a neutral grey, black or white) to 100 or more at the edge of the circle, which represents colors that have a very high chroma (saturation) or color purity. The h* axis represents hue. If a horizontal slice is taken through the center of the sphere, cutting the 'sphere' ('apple') in half, we see a colored circle. Around the edge of the circle we see every possible saturated color, or hue. This circular axis is known as h° for hue. The units are in the form of degrees° (or angles), ranging from 0° (red) through 90° (yellow), 180° (green), 270° (blue).

Figure 8:
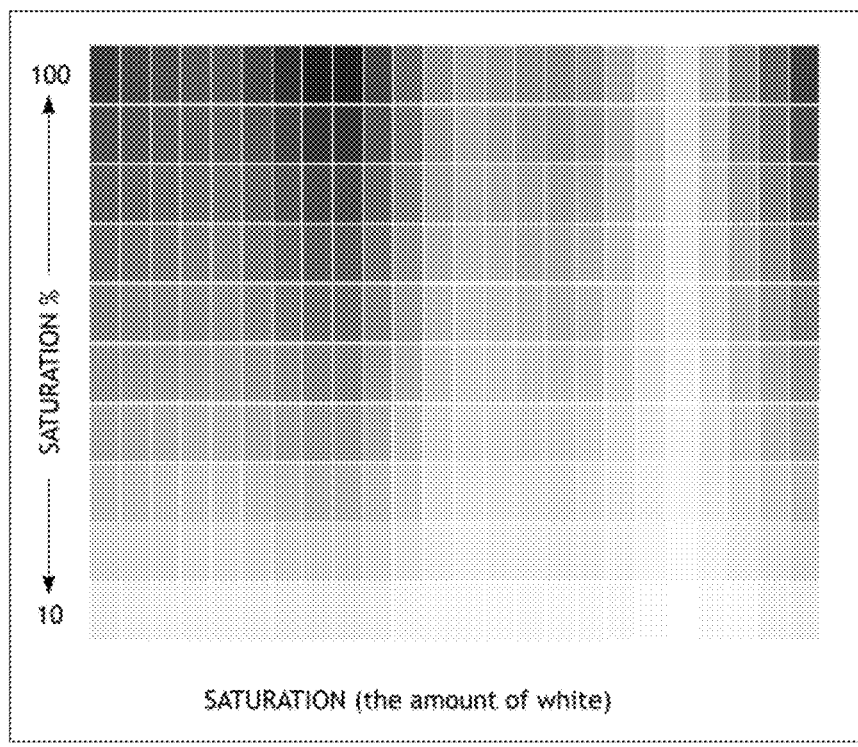
FIG. 8 is a chart illustrating various levels of color saturation.
Figure 9:
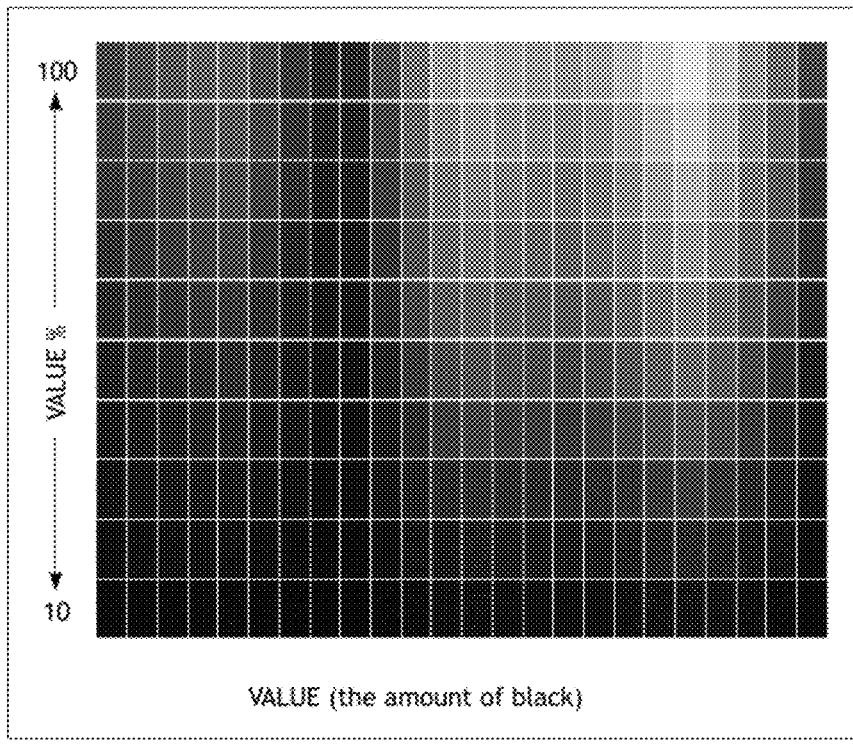
FIG. 9 is a chart illustrating various levels of color value.

Taking the color models discussed above into account, the present inventors have found that the specific combination of components present in the donning side layer (e.g., the second layer) of the glove can result in a layer that is a bright color without the layer exhibiting any "bleed out." Specifically, the donning side layer can exhibit sufficient levels of saturation and value so that the donning side layer appears bright and vivid, rather than washed out or overly dark. The saturation or chroma refers to the purity of a color. As shown in FIG. 8, on a scale of 0% to 100%, a high saturation % refers to a color that appears rich and full, while a low saturation % refers to a color that appears washed out, dull, and grayish. Referring to FIG. 8, as the amount of pure color decreases, the saturation % drops. For example, the colors shown on the top row in the chart of FIG. 8 have saturation of 100% and have no white, while the colors shown on the bottom row of the chart in FIG. 8 have a saturation of 0% and have high levels of white. In other words, as colors get very low in saturation % and approach 0% saturation, they become pastels. Meanwhile, value refers to the lightness or darkness of a color. As shown in FIG. 9, a low factor % refers to a color with high levels of black, while a high value % refers to a color with no black. For example, the colors shown on the top row in the chart of FIG. 9 have a value of 100% and have no black, while the colors shown on the bottom row in the chart of FIG. 9 have a value of 0% and have high levels of black. In other words, as the rows of colors move down the chart the value decreases, where more black is added until each color is essentially black. As mentioned above, due to the specific components of the second layer and the ratios at which they are present, the second layer of the glove of the present invention is able to exhibit a saturation level greater than about 25%, such as a saturation level greater than about 30%, such as a saturation level greater than about 40%, such as a saturation level greater than about 50%, such as a saturation level greater than about 60%, such as a saturation level greater than about 70%. For instance, in some preferred embodiments, the saturation level can range from about 50% to about 100%, such as from about 60% to about 100%, such as from about 70% to about 100%, such as from about 80% to about 100%. Further, the second layer of the glove of the present invention is able to exhibit a value level greater than about 25%, such as a value level greater than about 30%, such as a value level greater than about 40%, such as a value level greater than about 50%, such as a value level greater than about 60%, such as a value level greater than about 70%. For instance, in some preferred embodiments, the value level can range from about 50% to about 100%, such as from about 60% to about 100%, such as from about 70% to about 100%, such as from about 80% to about 100%. In addition, although it is preferred that the saturation and value levels be greater than about 25%, such levels may be more difficult to achieve. As such, saturation and value levels of less than about 25%, such as less than about 20%, such as less than about 15% are also contemplated in some embodiments of the present invention.

In addition, as a result of the specific components of each of the glove layers (e.g., the grip side layer and the donning side layer) and the processing conditions (e.g., dip times, coagulant concentrations, specific polymer formulations, etc.) by which the glove is made, the glove layers can have sufficient color contrast without "bleeding" or "muddying" of the darker color associated with one of the layers through the other lighter colored layer, while also being thin, which can maximize user comfort, enhance tactile sensitivity to temperature and surface textures, and reduce manufacturing time and cost. For instance, a glove made according to the present invention can have a palm thickness ranging from about 0.03 millimeters to about 0.20 millimeters, such as from about 0.06 millimeters (mm) to about 0.15 millimeters, such as from about 0.07 mm to about 0.14 mm, such as from about 0.08 millimeters to about 0.13 mm, such as from about 0.09 mm to about 0.12 mm. Further, the glove can have a cuff thickness ranging from about 0.03 to about 0.08 mm, such as from about 0.04 mm to about 0.07 mm, such as from about 0.05 mm to about 0.06 mm. In addition, the glove can have a finger thickness ranging from about 0.07 mm to about 0.17 mm, such as from about 0.08 mm to about 0.16 mm, such as from about 0.09 mm to about 0.15 mm. Moreover, the glove can have a length ranging from about 200 mm to about 625 mm, such as from about 220 mm to about 450 millimeters, such as from about 230 mm to about 260 mm, such as from about 235 mm to about 255 mm, such as from about 240 mm to about 250 mm. In still other embodiments and depending on the application for which the glove is used, the palm thickness, cuff thickness, and finger thickness can be at least about 0.01 mm, at least about 0.02 mm, at least about 0.03 mm, at least about 0.04 mm, or at least about 0.05 mm up to about 1 mm, up to about 2 mm, up to about 3 mm, up to about 4 mm, up to about 5 mm, or up to about 6 mm depending on the glove application, where thicker gloves may be required when the gloves are being used for protection from hazardous substances. Additionally, the glove can have a weight ranging from about 4 grams (g) to about 7 g, such as from about 4.5 g to about 6.5 g, such as from about 5 g to about 6 g.

Furthermore, an unaged glove made according to the present invention with a thickness of about 0.115 mm in the palm area can have a force-at-break ranging from about 8 Newtons (N) to about 15 N, such as from about 8.5 N to about 14 N, such as from about 9 N to about 13 N. Further, an unaged glove made according to the present invention with a thickness of about 0.115 mm in the palm area can have a tensile strength at break that ranges from about 20 MPa to about 50 MPa, such as from about 25 MPa to about 45 MPa, such as from about 28 MPa to about 40 MPa. Moreover, an unaged glove made according to the present invention with a thickness of about 0.115 mm in the palm area can have an elongation at break ranging from about 550% to about 750%, such as from about 575% to about 725%, such as from about 600% to about 700%. Additionally, at about 300% stretch-elongation, the modulus of an unaged glove made according to the present invention can range from about 1 MPa to about 7.5 MPa, such as from about 1.5 MPa to about 7 MPa, such as from about 2 MPa to about 6.5 MPa.

Meanwhile, a glove aged at 70° C.+/−2° C. for 168 hours+/−2 hours and having a thickness of about 0.115 mm in the palm area can have a force-at-break ranging from about 9 Newtons (N) to about 16 N, such as from about 9.5 N to about 15 N, such as from about 10 N to about 14 N. Further, the aged glove can have a tensile strength at break that ranges from about 25 MPa to about 50 MPa, such as from about 28 MPa to about 45 MPa, such as from about 30 MPa to about 42 MPa. Moreover, the unaged glove can have an elongation at break ranging from about 500% to about 700%, such as from about 525% to about 675%, such as from about 550% to about 650%. Additionally, at about 300% stretch-elongation, the modulus of the aged glove can range from about 1 MPa to about 7.5 MPa, such as from about 1.5 MPa to about 7 MPa, such as from about 2 MPa to about 6.5 MPa.

The precise point of measurement in order to determine that data described above is that defined in American Society for Testing and Materials (ASTM) test standard D-412-98a (Reapproved 2002), "Standard Test Methods for Vulcanized Rubber and Thermoplastic Elastomers—Tension, published January 2003, the contents of which are incorporated herein by reference. These test methods cover procedures used to evaluate the tensile (tension) properties of vulcanized thermoset rubbers and thermoplastic elastomers. The determination of tensile properties starts with test pieces taken from a sample material and includes the preparation of specimens and the testing of the specimens. Specimens may be in the shape of dumbbells, rings, or straight pieces of uniform cross-sectional area. Measurements of tensile stress, tensile stress at a given elongation, tensile strength, yield point, and ultimate elongation are made on specimens that have not been pre-stressed. Tensile stress, tensile strength, and yield point are based on the original cross-sectional area of a uniform cross-section of the specimen.

Various glove layer components, glove formation procedures, and several examples contemplated by the present invention are discussed in more detail below.

I. Glove Layers

The glove of the present invention may generally be formed from any of a variety of natural and/or synthetic elastomeric materials known in the art. For instance, some examples of suitable elastomeric materials include, but are not limited to, nitrile rubbers (e.g., acrylonitrile butadiene), polyurethanes, S-EB-S (styrene-ethylene-butylene-styrene) block copolymers, S-I-S (styrene-isoprene-styrene) block copolymers, S-B-S (styrene-butadiene-styrene) block copolymers, S-I (styrene-isoprene) block copolymers, S-B (styrene-butadiene) block copolymers, natural rubber latex, isoprene rubbers, chloroprene rubbers, neoprene rubbers, polyvinyl chlorides, silicone rubbers, and various combinations thereof.

In one particular embodiment, the grip side layer of the glove, the donning side layer of the glove, or both can be formed from a polyurethane. In another particular embodiment, the grip side layer of the glove, the donning side layer of the glove, or both can be formed from a nitrile rubber. In still another embodiment, the grip side layer can be formed from a polyurethane and the donning side layer can be formed from a nitrile rubber, or the grip side layer can be formed from a nitrile rubber and the donning side layer can be formed from a polyurethane. Various components of possible polyurethane formulations and nitrile rubber formulations contemplated by the present invention are discussed in more detail below, although it is to be understood that the polyurethane and nitrile rubber can be substituted for any other suitable elastomeric material, such as those mentioned above. For instance, the glove layers can also be formed from styrene-butadiene rubber, isobutylene-isoprene rubber, polychloroprene, polyisoprene, natural rubber, etc.

A. Polyurethane Formulation

The polyurethane that can be used to form one or more layers of the glove can be a film-forming thermoplastic polyurethane (e.g., an aliphatic-polyether or aliphatic-polyester type) or a polyether amides (e.g., Pebax®, which is available from Atochem North America, Inc. of Philadelphia, Pa.). Various types of polyurethane that may be suitable for use in the glove of the present invention are described in more detail in U.S. Pat. No. 4,888,829 to Kleinerman, et al. and U.S. Pat. No. 5,650,225 to Dutta, et al., which are incorporated herein in their entirety by reference thereto for all purposes.

The polyurethane can be compounded with various components based on 100 parts of the polyurethane. For instance, depending on whether the polyurethane formulation is used to form the grip side layer of the elastomeric glove of the present invention or the donning side layer of the elastomeric glove of the present invention, the polyurethane formulation of the present invention can include one or more of titanium dioxide or similar filler, a color pigment, or a combination thereof to provide a desired level of color, contrast, brightness, saturation, value, and/or opaqueness. Specifically, the compounded polyurethane formulation can include titanium dioxide or any other similar filler in an amount ranging from about 0.25 parts to about 15 parts, such as from about 0.5 parts to 12.5 parts, such as from about 0.75 parts to about 10 parts, based on 100 dry parts of the polyurethane. Without intending to be limited by any particular theory, the present inventors have found that the inclusion of titanium dioxide or any other similar filler in such amounts can prevent the bleed through of a color pigments between the various layers of the glove. Further, if utilized as the donning side layer of the elastomeric glove of the present invention, the compounded polyurethane formulation can include a lighter colored pigment (e.g., red, orange, yellow, green, blue, indigo, violet, or a combination thereof) in an amount ranging from about 0.25 parts to about 10 parts, such as from about 0.5 parts to 9 parts, such as from about 0.75 parts to about 8 parts, based on 100 dry parts of the polyurethane. The aforementioned colored pigments can provide more contrast with the outside environment than, for instance, a glove that includes a white donning side layer, where in many settings where gloves may be used, the outside environment is generally white (e.g., walls, countertops, equipment, reflections from light, etc.). Such an environment diminishes the ability of a white layered glove to serve as an adequate breach detector or indicator because the glove wearer will be less sensitive to observing a visual cue as to a breach. Meanwhile, if utilized as the grip side layer of the elastomeric glove of the present invention, the compounded polyurethane formulation can include a darker colored pigment (e.g., black, brown, dark gray, blue, purple, etc.) in an amount ranging from about 0.25 parts to about 5 parts, such as from about 0.5 parts to about 4 parts, such as from about 0.75 parts to about 3 parts, based on 100 dry parts of the polyurethane.

B. Nitrile Rubber Formulation

Meanwhile, the nitrile rubber that can be used to form one of the layers can include a carboxylated nitrile that is compounded with various components based on 100 parts of the carboxylated nitrile. The carboxylated nitrile rubber and the various components compounded with the nitrile rubber in the formulation of the present invention are discussed in more detail below.

Carboxylated nitrile, which is a terpolymer of butadiene, acrylonitrile, and organic acid monomers, has at least two properties that make it useful for manufacturing elastomeric articles. These two features are high strength and impermeability to certain hydrocarbon solvents and oils. Compounding and curing the rubber with other ingredients such as curing agents, accelerators, and activators is generally performed to optimize these properties. The level of each monomer in the polymer and the level of curing can affect the levels of strength and the chemical resistance in the finished article. Polymers with higher levels of acrylonitrile tend to have better resistance to aliphatic oils and solvents, but are also stiffer than polymers that have lower levels of acrylonitrile. While the chemical nature of the monomers from which the polymer is made offers some degree of chemical resistance, when the polymer molecules are chemically crosslinked, resistance to chemical swelling, permeation, and dissolution greatly increase.

The base polymer employed in the nitrile rubber can be a random terpolymer composition containing acrylonitrile, butadiene, and carboxylic acid components. It is believed that the particular advantageous properties of the present soft nitrile rubber materials can be due in part to the nature and interaction of a blend of acrylonitrile components in the composition. The blend can include two—a first and a second—acrylonitrile formulations in a compositional ratio ranging, respectively, from about 60:40 to 40:60. The orientation or placement of carboxyl groups on the nitrile polymer molecules—either outside or inside—can affect the reactivity of the carboxyl groups with zinc ions; hence, it is believed that some components exhibit softer, lower modulus properties and some components have good film forming properties.

The acrylonitrile content of the blended or combined terpolymer composition can range from about 17% by weight to about 45% by weight, such as from about 20% by weight to about 40% by weight, such as from about 20% by weight to about 35% by weight. In one embodiment, for instance, the acrylonitrile content can be between about 22% by weight and about 28% by weight, the methacrylic acid content can be less than about 10% by weight, and the remainder of the polymer can be butadiene. The methacrylic acid content should be less than about 15% by weight, preferably about 10% by weight, with butadiene making up the remainder balance of the polymer. The base terpolymer is made through a process of emulsion polymerization, and can be used while still in emulsion form to manufacture gloves or other elastomeric articles.

Further, the acrylonitrile polymer formulations that may be employed in the present invention can have a glass transition temperature ($T_g$) ranging from about −30° C. to about −10° C., such as from about −28° C. to about −12° C. In some embodiments, desirable nitrile polymer formulations, such as PolymerLatex X-1133 or Synthomer 6311 available from PolymerLatex GmbH, and Synthomer Ltd., respectively, can have a $T_g$ between about −26° C. and about −18° C. Other nitrile formulations, such as Nantex® 635t, commercially available from Nantex Industry Co., Ltd. (Taiwan, R.O.C.), can have a $T_g$ between about −25.5° C. and about −23.4° C. Another suitable nitrile polymer contemplated for use in the elastomeric articles of the present invention is Lutex 111 manufactured by LG Chem, which has a $T_g$ ranging from about −22° C. to about −14° C. and a total solids content of about 44.5% to about 45.5% and a pH of from about 8.2 to about 8.8.

It is believed, however, that the nitrile butadiene polymer properties do not come from components of the nitrile material, but from the structure of the polymer, which in turn, is determined by polymerization conditions. Polymer properties are very much affected by the polymer structure. Molecular structure of polymers can be very complex, with variability in molecular weight, molecular weight distribution, amount of branching, amount of crosslinking during polymerization, many possible types of chemical addition for diene monomers, etc. When several monomer types are combined into a polymer such as in a carboxylated acrylonitrile butadiene polymer used for glove manufacture, the structure becomes even more complex. Overall levels of each monomer type and the sequencing of the monomer units also contribute to the properties of the resulting polymer. When the repeating structure of the monomer units is random, such as in the nitrile rubber used for gloves, the physical properties of the polymer have increased influence from the polymer linearity (vs. branching) and molecular weight as compared to the properties of a homopolymer. This is because the properties expected from a regular repeating structure of a polymer made only from each single monomer change once that repeating structure is interrupted or otherwise altered by the addition of other types of monomer units. A high level of any particular monomer will likely increase the chance of contributing properties expected from a homopolymer made from that monomer, due to increased similarity of the repeating structures.

In carboxylated nitrile rubber used for thin glove manufacture, the acrylonitrile and carboxylic acid, which typically total approximately 35% by weight, add some plastic like character to the polymer with respect to resilience, permanent set, and stress relaxation. They also prevent a regular cis-1,4 repeating structure that would give polybutadiene its highest resilience and lowest set/relaxation.

A general description of such a carboxylated nitrile rubber would be a long-chain random arrangement of its three component monomers, with branching and crosslinking. These branched, random terpolymers are former into discrete tiny particles that are emulsified in water. In addition to the polymer structure, the particle structure also plays a part in the final properties of a glove. Parameters such as particle size, particle size distribution, level of particle agglomeration, particle density, etc., affect how the product is formed, and also its eventual properties.

Although not required, the polymer structure can include a random terpolymer (as opposed to block or alternating terpolymer) of acrylonitrile, butadiene, and carboxylic acid. The properties depend on the average molecular weight, the molecular weight distribution, the linearity or degree of branching, the gel content (crosslinking during polymerization), and the microstructure (which monomer units are next to each other in short sections of the polymer chain).

Regardless of the particular structure of the nitrile rubber that can be used in one or more layers of the glove of the present invention, various additional components can be incorporated during the compounding of the nitrile rubber formulation so that the overall glove can have certain desired properties.

For instance, an alkali agent can be added to the nitrile rubber formulation to adjust the pH of the nitrile rubber formulation. Any suitable alkali agent can be used, and, in some embodiments, the alkali agent can be potassium hydroxide, ammonium hydroxide, or a combination thereof. In any event, the alkali agent can be used to adjust the nitrile rubber formulation to a pH that can range from about 9 to about 11, such as from about 9.2 to about 10.5, such as from about 9.5 to about 10.2. In addition to acting as a pH adjuster, the alkali agent can be utilized in combination with a metal oxide as discussed below to facilitate the formation of a nitrile rubber formulation that has high strength. Specifically, the alkali agent can include monovalent ions, such as K, Na, or H, which, although they do not have sufficient electron capacity to accommodate a bond with a second methylacrylic acid unit, may allow for weaker forms of associative bonding. As such, the alkali agents (e.g., monovalent salts) that can be used to increase the pH of the nitrile rubber formulation may also swell the nitrile rubber particles, making more carboxylic acid groups accessible to other crosslinking agents, such as the metal oxides discussed in more detail below. The positive charge of the cation can well balance the negative electrons of the acidic carboxyl groups.

Regardless of the particular alkali agent utilized, the alkali agent can be present in the compounded nitrile rubber formulation in an amount ranging from about 0.1 parts to about 2 parts, such as from about 0.25 parts to about 1.75 parts, such as from about 0.5 parts to about 1.5 parts, based on 100 dry parts of the nitrile rubber.

Further, the nitrile rubber formulation that can be used in one or more layers of the elastomeric glove of the present invention can be chemically crosslinked to enhance the elasticity, strength, and chemical resistance of the nitrile rubber formulation. Crosslinking can be accomplished in at least two ways: the butadiene subunits can be covalently crosslinked with sulfur and accelerators, while the carboxylated (organic acid) sites can be ionically crosslinked with metal oxides or salts. Ionic crosslinks, resulting from, for example, the addition of a metal oxide, such as zinc oxide, to the nitrile rubber formulation, can result in a nitrile rubber formulation having high tensile strength, puncture resistance, and abrasion resistance, as well as high elastic modulus (a measure of the force required to stretch a film of the rubber), but poor oil and chemical resistance, which is why a sulfur crosslinking agent can be added to the nitrile rubber formulation, as discussed in more detail below.

Including a metal oxide, such as zinc oxide, in the nitrile rubber formulation can improve the dipping qualities and cure rates of the formulation. In contrast, when zinc oxide is not employed, the curing time required to reach an optimum state of cure can be much longer and the curing may be less efficient. This means that the crosslinks are longer (more sulfur atoms per crosslink) and there may be a higher amount of sulfur that does not crosslink polymer chains. The result can be a less-effectively cured rubber that has lowered heat resistance and less chemical resistance.

While not intending to be bound by theory, it is believed that the matrix structure and strength of the nitrile rubber formulation that can be used in one or more layers of the glove of the present invention may result from the interaction of all ions present in the system, in particular, divalent or higher valence cations, with the carboxylic acid components of the polymer matrix. Divalent or multivalent cations, such as Mg, Ca, Zn, Cu, Ti, Cd, Al, Fe, Co, Cr, Mn, and Pb, can crosslink with the carboxyl groups of the ionized carboxylic acids, forming relatively stable bonds. Of these cation species, Mg, Ca, Zn, Cu, or Cd are more desirable. Preferably, the methylacrylic acid monomers are located relatively close to each other in the polymer matrix structure; in such a fashion, the divalent or multivalent cation can crosslink with two or more nearby acid units. The positive charge of the cation can well balance the negative electrons of the acidic carboxyl groups. It is believed that, absent divalent or multivalent cations, multiple polymer chains in the nitrile emulsions are not well crosslinked together.

Regardless of the particular metal oxide utilized, the metal oxide can be present in the compounded nitrile rubber formulation in an amount ranging from about 0.1 parts to about 2 parts, such as from about 0.25 parts to about 0.4 parts, such as from about 0.08 parts to about 0.3 parts, based on 100 dry parts of the nitrile rubber.

As mentioned above, a sulfur crosslinking agent can also be used in the nitrile rubber formulation to provide oil and chemical resistance to a layer of a glove containing the formulation. Such crosslinking can provide resistance to chemical swelling, permeation, and dissolution. In contrast to the alkali agent and metal oxide crosslinking agents discussed above, the sulfur is used to covalently crosslink the butadiene subunits of the carboxylated nitrile rubber.

Sulfur can be present in the compounded nitrile rubber formulation in an amount ranging from about 0.1 parts to about 5 parts, such as from about 0.2 parts to about 2.5 parts, such as from about 0.5 parts to about 2 parts, based on 100 dry parts of the nitrile rubber.

A vulcanization accelerator can be used in combination with the sulfur crosslinking agent to provide the desired level of chemical resistance to the nitrile rubber formulation. As with the sulfur crosslinking agent, the vulcanization accelerator can be used to covalently crosslink the butadiene subunits of the carboxylated nitrile rubber. The vulcanization accelerator can be a single dithiocarbamate accelerator that is added with sulfur. However, in other cases where higher levels of chemical resistance are needed, a combination of vulcanization accelerators can be utilized. Such a combination can include a dithiocarbamate, a thiazole, and a guanidine compound, which can be present according to a ratio of about 1:2:2. For example, the vulcanization accelerator can be zincediethyldithiocarbamate (ZDEC), zinc mercaptobenzothiazole (ZMBT), diphenyl guanidine (DPG), or a combination thereof.

Regardless of the particular vulcanization accelerator or combination of vulcanization accelerators utilized, the vulcanization accelerator can be present in the compounded nitrile rubber formulation in an amount ranging from about 0.1 parts to about 5 parts, such as from about 0.2 parts to about 2.5 parts, such as from about 0.5 parts to about 2 parts, based on 100 dry parts of the nitrile rubber. In one particular embodiment, the compounds can be zincdiethyldithiocarbamate (ZDEC), zinc mercaptobenzothiazole (ZMBT), and diphenyl guanidine (DPG), at about 0.25 parts ZDEC, 0.5 parts ZMBT, and 0.5 parts DPG, based on 100 dry parts of nitrile rubber. In another particular embodiment, the compounds can be zincdiethyldithiocarbamate (ZDEC), zinc mercaptobenzothiazole (ZMBT), and diphenyl guanidine (DPG), at about 0.25 parts ZDEC, 0.25 parts ZMBT, and 0.5 parts DPG, based on 100 dry parts of nitrile rubber.

Moreover, depending on whether the nitrile rubber formulation is used to form the grip side layer of the elastomeric glove of the present invention or the donning side layer of the elastomeric glove of the present invention, the nitrile rubber formulation of the present invention can include one or more of a titanium dioxide or similar filler, a color pigment, or a combination thereof to provide a desired level of color, contrast, brightness, saturation, value, and/or opaqueness. Specifically, the compounded nitrile rubber formulation can include titanium dioxide or any other similar filler in an amount ranging from about 0.25 parts to about 30 parts, such as from about 0.5 parts to 15 parts, such as from about 0.75 parts to about 10 parts, based on 100 dry parts of the nitrile rubber. Without intending to be limited by any particular theory, the present inventors have found that the inclusion of titanium dioxide or any other similar filler in such amounts can prevent the bleed through of a color pigments between the various layers of the glove. Further, if utilized as the donning side layer of the elastomeric glove of the present invention, the compounded nitrile rubber formulation can include a lighter colored pigment (e.g., red, orange, yellow, green, blue, indigo, violet, or a combination thereof) in an amount ranging from about 0.5 parts to about 15 parts, such as from about 0.5 parts to about 12.5 parts, such as from about 0.6 parts to 9 parts, such as from about 0.8 parts to about 8 parts, based on 100 dry parts of the nitrile rubber. Moreover, the present inventors have discovered that the ratio of the parts of titanium dioxide to the colored pigment in the donning side layer of the formulation (e.g., nitrile rubber) can be controlled to achieve a donning side layer having sufficient value and saturation percentages as discussed above. Specifically, the ratio of parts of titanium dioxide to the parts of colored pigment in the donning side layer formulation can range from about 0.25 to about 3, such as from about 0.3 to about 2.75, such as from about 0.75 to about 2.5, such as from about 1 to about 2. It should be understood, however, that in some embodiments, the compounded nitrile rubber formulation used as the donning side layer of the elastomeric glove can include titanium dioxide in the amounts described above without the inclusion of an additional colored pigment. It should also be understood that in some embodiments, the layer described as the donning side layer can form the grip side layer and vice versa.

Meanwhile, if utilized as the grip side layer of the elastomeric glove of the present invention, the compounded nitrile rubber formulation can include a darker colored pigment (e.g., black, brown, dark gray, blue, purple, etc.) in an amount ranging from about 0.25 parts to about 5 parts, such as from about 0.5 parts to about 4 parts, such as from about 0.75 parts to about 3 parts, based on 100 dry parts of the nitrile rubber.

However, it is also to be understood that the formulation used to form the donning side layer of the glove can alternatively be used to form the grip side layer of the glove, and the formulation used to form the grip side layer of the glove can alternatively be used to form the donning side layer of the glove, where breach detection can still be determined due to the contrast in color between the layers.

Regardless of the specific components utilized to form the formulations of the present invention, after compounding, the resulting formulations can each have a total solids content (TSC) a TSC of from about 15% to about 30%, such as from about 16% to about 28%, such as from about 18% to about 26%. The reduction of the TSC enables for the manufacture of multi-layered articles that have a reduced thickness compared to some other multi-layered articles. Further, it is to be understood that the components of the polyurethane formulation and the nitrile rubber formulation can be compounded by adding them to the polyurethane formulation or the nitrile rubber formulation in any order.

After the polyurethane and nitrile rubber formulations are compounded, the formulations can be used to form various layers of any suitable elastomeric article. In one particular embodiment, the polyurethane formulation, nitrile rubber formulation, or a combination thereof can be used to form a glove having multiple layers to facilitate breach detection, as discussed in more detail below.

II. Glove Formation

After the various glove layer formulations (e.g., the polyurethane and nitrile rubber formulations or formulations formed from any other suitable materials) are compounded, the formulations can be used in a coagulant dip-coating process to form an elastomeric glove. Although any suitable materials can be utilized to form the multilayered glove, in one particular embodiment, the grip side layer can be formed from polyurethane and the donning side layer can be formed from nitrile rubber. For simplicity, the following glove forming dip processes are described in terms of the formation of a glove having a polyurethane grip side layer and a nitrile rubber donning side layer, although it is to be understood that the grip side layer can be nitrile rubber and the donning side layer can be polyurethane, where it is also contemplated that any suitable materials can be substituted for the grip side layer and the donning side layer. For instance, both layers can be formed from nitrile rubber formulations.

Figure 3:
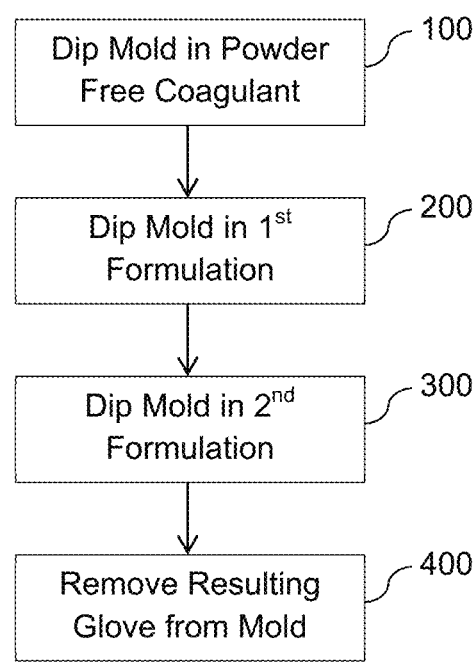
FIG. 3 illustrates a method of forming the multilayered glove according to one embodiment of the present invention involving a three-dip process.

As shown in FIG. 3, in one particular embodiment, a three-dip process is contemplated that includes steps 100, 200, 300, and 400. The process for forming an elastomeric glove entails providing a clean glove form or mold that can be preheated to approximately 55-60° C., and preferably about 58° C. In step 100, the prepared mold is then dipped into a solution (e.g., an aqueous solution) comprising a powder free coagulant that includes one or more metallic salts (e.g., nitrate, sulfate, or chloride salts of calcium, aluminum, or zinc, or a combination thereof). The dip time for the solution can range from less than about 2 seconds to up to about 60 seconds. In one particular embodiment, a dip time between about 3 seconds and 10 seconds is desirable. For instance, the dip time can be about 5 seconds. The metallic salts can be present in the solution in an amount ranging from about 3 wt. % to about 22 wt. %, such as from about 4 wt. % to about 21 wt. %, such as from about 5 wt. % to about 20 wt. % based on the total weight of the solution. In addition to a powder free coagulant, the solution in step 100 can include one or more other components. For instance, the solution can include a wax, a hydrogel, a silicone, a gel, an inorganic powder (e.g., carbonates, stearates, oxides, hydroxides, aluminates, etc.), an antimicrobial agent (e.g., silver ($Ag^{++}$), copper ($Cu^{++}$), polyhexamethylene biguanide (PHMB), etc.), an acrylic polymer, a peroxide crosslinking agent, an emollient (e.g., shea butter, petroleum, etc.), a hydrophilic agent, a hydrophobic agent, a pigment, a colorant, a dye, a polyolefin-based powder (e.g., a polyethylene powder or a polypropylene powder), a surfactant, a soap, an acidic agent, an alkali agent, or a combination thereof. These additional components can be present in the solution in an amount ranging from about 0.1 wt. % to about 30 wt. %, such as from about 0.5 wt. % to about 25 wt. %, such as from about 1 wt. % to about 20 wt. % based on the total weight of the solution.

In step 200, the mold, with the powder free coagulant on its surface, can be dried and reheated to approximately 70° C.±5° C., and dipped into a bath of a first formulation (e.g., the compounded polyurethane formulation) to form a first layer (e.g., a grip side layer) of a gelled glove. The dip time for the first formulation can range from less than about 2 seconds to up to about 60 seconds. In one particular embodiment, a dip time between about 3 seconds and 10 seconds is desirable. For instance, the dip time can be about 5 seconds.

Then, in step 300, the mold with the first layer (e.g., grip side layer) coated thereon, can be dried and reheated to approximately 70° C.±5° C., and dipped into a bath of a second formulation (e.g., the compounded nitrile rubber formulation) one or more times (e.g., 1, 2, 3, or 4 times) to form a second layer (e.g., the donning side layer) of a gelled glove. In some embodiments, in dip step 300, the mold can be dipped into the second formulation (e.g., the compounded nitrile rubber formulation) so that the second formulation does not extend past the polyurethane layer on the mold so that no separately identifiable cuff is formed when the resulting glove is removed from the mold. In other embodiments, in dip step 300, the mold can be dipped into the second formulation so that the second formulation extends past the first layer on the mold so that a cuff formed from the second formulation is visible when the resulting glove is removed from the mold. The dip time for the second formulation can range from less than about 5 seconds to up to about 60 seconds. In one particular embodiment, a dip time between about 6 seconds and 15 seconds is desirable. For instance, the dip time can be about 8 seconds. As such, the dip time for the second formulation can be longer than the dip time for the first formulation. For instance, the dip time for the second formulation can be from about 40% to about 100%, such as from about 50% to about 80%, such as about 60% longer than the dip time for the first formulation. Without intending to be limited to any particular theory, the present inventors have found that by utilizing a longer dip time for the second formulation as compared to the first formulation in a 3-dip process where no coagulant dip is performed between the first formulation dip and the second formulation dip, the resulting glove can include layers having acceptable levels of hue and saturation, where color bleed through is minimal and where sufficient levels of contrast exist between the layers formed by the first formulation and the second formulation. As a result, the ability to detect breaches in the glove can be enhanced. Further, regardless of whether or not a separate cuff layer is formed, the mold with the two layered gelled glove substrate applied thereon with the donning side layer on its outermost surface can then be soaked in water to remove all of the water-soluble material components. The mold with the gelled glove substrate applied thereon can then be dried in an oven at a temperature ranging from about 80° C. to about 100° C. Afterwards, in step 400, the glove is removed from the mold, and the glove surfaces can thereafter be treated with chlorinated water to reduce the tackiness of the glove surfaces. Finally, the resulting gloves are dried, stripped from the former, and readied for packaging.

Figure 4:
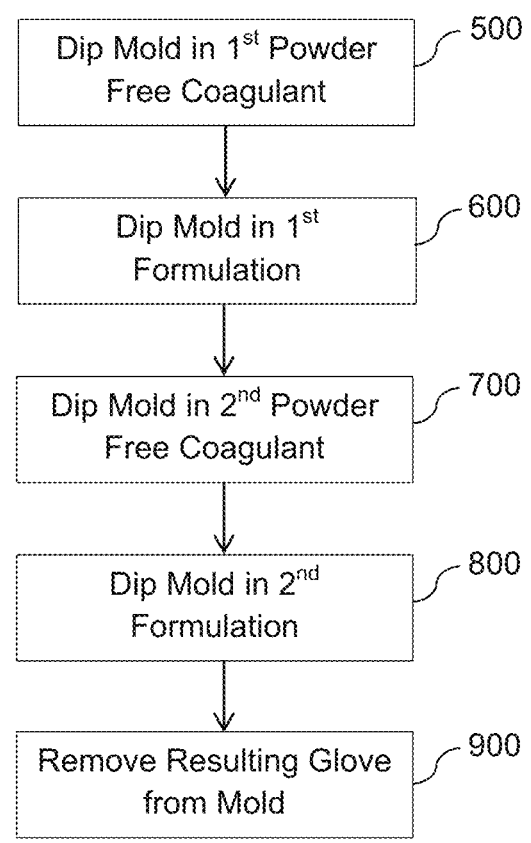
FIG. 4 illustrates a method of forming the multilayered glove according to another embodiment of the present invention involving a four-dip process.

As shown in FIG. 4, in another particular embodiment, a four-dip process is contemplated that includes steps 500, 600, 700, 800 and 900. The process for forming an elastomeric glove entails providing a clean glove form or mold that can be preheated to approximately 55-60° C., and preferably about 58° C. In step 500, the prepared mold is then dipped into a solution (e.g., an aqueous solution) comprising a first powder free coagulant that includes one or more metallic salts (e.g., nitrate, sulfate, or chloride salts of calcium, aluminum, or zinc, or a combination thereof). The dip time for the solution can range from less than about 2 seconds to up to about 60 seconds. In one particular embodiment, a dip time between about 3 seconds and 10 seconds is desirable. For instance, the dip time can be about 5 seconds. The metallic salts can be present in the solution in an amount ranging from about 6 wt. % to about 14 wt. %, such as from about 7 wt. % to about 13 wt. %, such as from about 8 wt. % to about 12 wt. % based on the total weight of the solution. In addition to a first powder free coagulant, the solution in step 500 can include one or more other components. For instance, the solution can include a wax, a hydrogel, a silicone, a gel, an inorganic powder (e.g., carbonates, stearates, oxides, hydroxides, aluminates, etc.), an antimicrobial agent (e.g., silver ($Ag^{++}$), copper ($Cu^{++}$), polyhexamethylene biguanide (PHMB), etc.), an acrylic polymer, a peroxide crosslinking agent, an emollient (e.g., shea butter, petroleum, etc.), a hydrophilic agent, a hydrophobic agent, a pigment, a colorant, a dye, a polyolefin-based powder (e.g., a polyethylene powder or a polypropylene powder), a surfactant, a soap, an acidic agent, an alkali agent, or a combination thereof. These additional components can be present in the solution in an amount ranging from about 0.1 wt. % to about 30 wt. %, such as from about 0.5 wt. % to about 25 wt. %, such as from about 1 wt. % to about 20 wt. % based on the total weight of the solution.

In step 600, the mold, with the first powder free coagulant on its surface, is dried and reheated to approximately 70° C.±5° C., and dipped into a bath of a first formulation (e.g., the compounded polyurethane formulation) to form a first layer (e.g., the grip side layer) of a gelled glove. The dip time for the first formulation can range from less than about 2 seconds to up to about 60 seconds. In one particular embodiment, a dip time between about 3 seconds and 10 seconds is desirable. For instance, the dip time can be about 5 seconds.

Then, in step 700, the mold with the first layer coated thereon is dipped into a solution (e.g., an aqueous solution) comprising a second powder free coagulant that includes one or more metallic salts (e.g., nitrate, sulfate, or chloride salts of calcium, aluminum, or zinc, or a combination thereof). The dip time for the solution can range from less than about 0.1 seconds to up to about 60 seconds. In one particular embodiment, a dip time between about 0.25 seconds and 10 seconds is desirable. For instance, the dip time can be about 0.5 seconds. The metallic salts can be present in the solution in an amount ranging from about 3 wt. % to about 22 wt. %, such as from about 4 wt. % to about 21 wt. %, such as from about 5 wt. % to about 20 wt. % based on the total weight of the solution, which can facilitate formation of a sufficient barrier between the first layer and the second layer to stop or prevent infiltration of the color from the first layer into the second layer, yet the glove can still have a reduced thickness compared to commercially available gloves. In addition to a second powder free coagulant, the solution in step 700 can include one or more other components. For instance, the solution can include a wax, a hydrogel, a silicone, a gel, an inorganic powder (e.g., carbonates, stearates, oxides, hydroxides, aluminates, etc.), an antimicrobial agent (e.g., silver ($Ag^{++}$), copper ($Cu^{++}$), polyhexamethylene biguanide (PHMB), etc.), an acrylic polymer, a peroxide crosslinking agent, an emollient (e.g., shea butter, petroleum, etc.), a hydrophilic agent, a hydrophobic agent, a pigment, a colorant, a dye, a polyolefin-based powder (e.g., a polyethylene powder or a polypropylene powder), a surfactant, a soap, an acidic agent, an alkali agent, or a combination thereof. These additional components can be present in the solution in an amount ranging from about 0.1 wt. % to about 30 wt. %, such as from about 0.5 wt. % to about 25 wt. %, such as from about 1 wt. % to about 20 wt. % based on the total weight of the solution.

Next, in step 800, the mold can be dried and reheated to approximately 70° C.±5° C., and dipped into a bath of a second formulation (e.g., the compounded nitrile rubber formulation) one or more times (e.g., 1, 2, 3, or 4 times) to form a second layer (e.g., the donning side layer). The dip time for the second formulation can range from less than about 0.5 seconds to up to about 60 seconds. In one particular embodiment, a dip time between about 1 second and 8 seconds is desirable. For instance, the dip time can be about 3 seconds. As such, the dip time for the second formulation can be shorter than the dip time for the first formulation. Specifically, the dip time for the second formulation can be from about 10% to about 90%, such as from about 15% to about 80%, such as from about 20% to about 60%, such as about 40% shorter than the dip time for the first formulation. Without intending to be limited to any particular theory, the present inventors have found that by utilizing a second coagulant dip having a dip time as low as about 0.1 seconds and a shorter dip time for the second formulation as compared to the first formulation in a 4-dip process, the resulting glove can include layers having acceptable levels of hue and saturation, where color bleed through is minimal and where sufficient levels of contrast exist between the layers formed by the first formulation and the second formulation. As a result, the ability to detect breaches in the glove is enhanced. Further, although four dips are utilized, the time to manufacture the glove can, in some embodiments, be reduced compared to a three-dip process as described above, which may utilize a second formulation dip that requires more time than the combined time required to complete the second coagulant dip and second formulation dip in the four-dip process as described above. Further, despite utilizing a 4-dip process, the glove can still have a reduced thickness compared to commercially available gloves.

In some embodiments, in dip step 800, the mold can be dipped into the second formulation so that the second formulation does not extend past the first layer on the mold so that no separately identifiable cuff is formed when the resulting glove is removed from the mold. In other embodiments, in dip step 800, the mold can be dipped into the compounded second formulation so that the compounded second formulation extends past the first layer on the mold so that a separately identifiable cuff formed from the second formulation is visible when the resulting glove is removed from the mold. Regardless of whether or not a cuff is formed, the mold with the two layered gelled glove substrate applied thereon can then be soaked in water to remove all of the water-soluble material components. The mold with the gelled glove substrate applied thereon can then dried in an oven at a temperature ranging from about 80° C. to about 100° C. Afterwards, in step 900, the glove is removed from the mold, and the glove surfaces can thereafter be treated with chlorinated water to reduce the tackiness of the glove surfaces. Finally, the resulting gloves are dried, stripped from the former, and readied for packaging. Without intending to be limited by any particular theory, the present inventors have found that utilizing metallic salt at such increased amounts in step 700 can facilitate the formation of a glove having two distinct layers where there is clear separation between the two formulation layers (e.g., the grip side layer and the donning side layer). In other words, the increased amount of metallic salt can create a sufficient barrier between the layers to prevent infiltration of the darker pigment or color in one of the layers into the layer that includes the lighter pigment or color in order to maintain a sufficient level of contrast between the layers.

Figure 5:
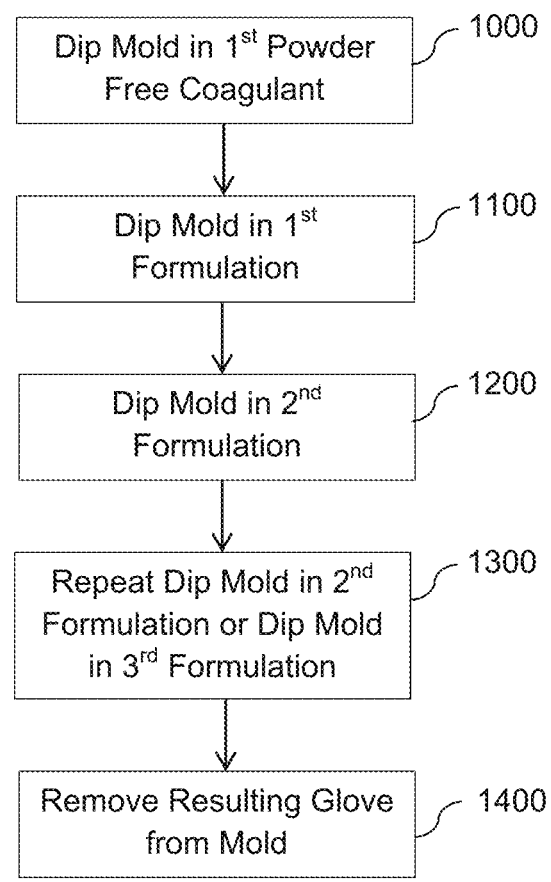
FIG. 5 illustrates a method of forming the multilayered glove according to another embodiment of the present invention involving an alternative four-dip process.

In an another method contemplated by the present invention, as shown in FIG. 5, an alternative four-dip process is contemplated that includes steps 1000, 1100, 1200, 1300, and 1400. The process for forming an elastomeric glove entails providing a clean glove form or mold that can be preheated to approximately 55-60° C., and preferably about 58° C. In step 1000, the prepared mold is then dipped into a solution (e.g., an aqueous solution) comprising a powder free coagulant that includes one or more metallic salts (e.g., nitrate, sulfate, or chloride salts of calcium, aluminum, or zinc, or a combination thereof). The dip time for the solution can range from less than about 2 seconds to up to about 60 seconds. In one particular embodiment, a dip time between about 3 seconds and 10 seconds is desirable. For instance, the dip time can be about 5 seconds. The metallic salts can be present in the solution in an amount ranging from about 3 wt. % to about 22 wt. %, such as from about 4 wt. % to about 21 wt. %, such as from about 5 wt. % to about 20 wt. % based on the total weight of the solution. In addition to a powder free coagulant, the solution in step 1000 can include one or more other components. For instance, the solution can include a wax, a hydrogel, a silicone, a gel, an inorganic powder (e.g., carbonates, stearates, oxides, hydroxides, aluminates, etc.), an antimicrobial agent (e.g., silver ($Ag^{++}$), copper ($Cu^{++}$), polyhexamethylene biguanide (PHMB), etc.), an acrylic polymer, a peroxide crosslinking agent, an emollient (e.g., shea butter, petroleum, etc.), a hydrophilic agent, a hydrophobic agent, a pigment, a colorant, a dye, a polyolefin-based powder (e.g., a polyethylene powder or a polypropylene powder), a surfactant, a soap, an acidic agent, an alkali agent, or a combination thereof. These additional components can be present in the solution in an amount ranging from about 0.1 wt. % to about 30 wt. %, such as from about 0.5 wt. % to about 25 wt. %, such as from about 1 wt. % to about 20 wt. % based on the total weight of the solution. In step 1100, the mold, with the powder free coagulant on its surface, can be dried and reheated to approximately 70° C.±5° C., and dipped into a bath of a first formulation (e.g., the compounded polyurethane formulation) to form a first layer (e.g., a grip side layer) of a gelled glove. The dip time for the first formulation can range from less than about 2 seconds to up to about 60 seconds. In one particular embodiment, a dip time between about 3 seconds and 10 seconds is desirable. For instance, the dip time can be about 5 seconds. Then, after allowing for sufficient time (e.g., ranging from less than about 5 seconds up to about 60 seconds, and, desirably, ranging from about 5 seconds and 10 seconds) to ensure that the first formulation is not flowing, in step 1200, the mold with the first layer (e.g., grip side layer) coated thereon can be dried and reheated to approximately 70° C.±5° C., and dipped into a bath of a second formulation (e.g., the compounded nitrile rubber formulation) one time to form a first part of a second layer (e.g., the donning side layer) of a gelled glove. The dip time for the second formulation can range from less than about 2 seconds to up to about 60 seconds. In one particular embodiment, a dip time between about 3 seconds and 10 seconds is desirable. For instance, the dip time can be about 5 seconds.

Next, in step 1300, the mold with the first layer (e.g., grip side layer) and the first part of the second layer (e.g., the donning side layer) coated thereon can be dipped in the second formulation for a second time, or, can be dipped into a third formulation, where step 1300 can ensure that the desired saturation and value levels discussed above are achieved. Again, the dip time for the second dip of the second formulation or the dip of the third formulation can range from less than about 2 seconds to up to about 60 seconds. In one particular embodiment, a dip time between about 3 seconds and 10 seconds is desirable. For instance, the dip time can be about 5 seconds. Additionally, the time lapse between the dip in step 1200 and the dip in step 1300 can range from less than about 5 seconds to about 60 seconds, and desirably from about 5 seconds to about 10 seconds to ensure that the formulation from step 1200 is not flowing when the dip in step 1300 occurs. In some embodiments, in dip steps 1200-1300, the mold can be dipped into the formulations (e.g., the compounded nitrile rubber formulation) so that the formulations do not extend past the polyurethane layer on the mold so that no separately identifiable cuff is formed when the resulting glove is removed from the mold, where the glove can then be folded over to form a cuff where the donning side layer is exposed. In other embodiments, in dip steps 1200-1300, the mold can be dipped into the formulations so that the formulations extends past the first layer on the mold so that a cuff formed from the formulations in steps 1200-1300 is visible when the resulting glove is removed from the mold. Regardless of whether or not a separate cuff layer is formed, the mold with the two layered gelled glove substrate applied thereon with the donning side layer on its outermost surface can then be soaked in water to remove all of the water-soluble material components. The mold with the gelled glove substrate applied thereon can then be dried in an oven at a temperature ranging from about 80° C. to about 100° C. Afterwards, in step 1400, the glove is removed from the mold, and the glove surfaces can thereafter be treated with chlorinated water to reduce the tackiness of the glove surfaces. Finally, the resulting gloves are dried, stripped from the former, and readied for packaging.

During the aforementioned dip processes, faster entry and exit speeds of the glove mold into the polyurethane and/or nitrile rubber formulation dipping solutions can provide a more even thickness profile to the glove, due at least in part to the reduced difference in residence time of the fingertip and cuff areas of the molds in the compounded formulations. The mold can be extracted from the dip bath at or near an initial vertical position and raised such that the finger tips are elevated to a horizontal or greater than horizontal position (e.g., tilted to an angle of about 20° to 45° above horizontal) for a brief period of time ranging from a few seconds to about 40 seconds. Quickly thereafter, the finger tips can be lowered to a position or angle between horizontal and initial vertical, while rolling the mold along its longitudinal axis. The raising and lowering action can be repeated in a sinusoidal or wave-like motion. This process can enable the elastomeric material formulations (e.g., the polyurethane formulations and nitrile rubber formulations) to distribute more evenly over the mold or former and produce a substrate product that is thinner overall.

In addition, in some embodiments, whether a three-dip process or a four-dip process is utilized, during the dip of the first formulation (e.g., to form the first or grip side layer) a mask can be utilized to form any desired graphic, pattern, logo, design, or text, etc. on the exterior grip side layer of the glove, where the layer associated with the donning side of the glove is visible in the locations where the mask is applied after dipping the mold with the first (grip side) layer in the second formulation to form the second (donning side) layer.

The present invention may be better understood with reference to the following examples.

III. EXAMPLES

Example 1

In Example 1, elastomeric gloves were made using a polyurethane formulation and a nitrile rubber formulation via the 4-step coagulant dip-coating process described above and then subjected to mechanical testing. The polyurethane and nitrile rubber formulations utilized are described in more detail in Tables 2 and 3 below. The first coagulant dip (the dip step prior to the polyurethane dip) included 12 wt. % calcium nitrate, while the second coagulant dip (the dip step after the polyurethane dip and before the nitrile rubber dip) included 18 wt. % calcium nitrate. Gloves were formed so that the nitrile rubber layer extended past the polyurethane layer to form a cuff, and their mechanical properties were compared to conventional purple nitrile gloves. The tensile testing parameters and methods are defined in American Society for Testing and Materials (ASTM) test standard D-412-98a. In the present invention, the ASTM protocol was employed with no changes. The testing apparatus used was an Intron® tonometer, model 5564, with a static load cell of capacity about +/−100N, and a XL extensometer. However, it is to be understood that other similar kinds of equipment could be used, as long as the machine met the requirements of the ASTM standard.

TABLE 2

Grip Side Layer

| Component | Parts Per 100 Parts of Polyurethane |
|---|---|
| Polyurethane | 100 |
| Titanium Dioxide | 1 |
| Blue Pigment | 1.5 |
| Total Solids Content | 24% |

TABLE 3

Donning Side Layer

| Component | Parts Per 100 Parts of Nitrile Rubber |
|---|---|
| Nitrile Rubber | 100 |
| Potassium Hydroxide | 1.4 |
| Zinc Oxide | 1.35 |
| Sulfur | 1 |
| ZDEC | 0.25 |
| DPG | 0.5 |
| ZMBT | 0.5 |
| Titanium Dioxide | 1 |
| Green Pigment | 1 |
| Total Solids Content | 21% |

The gloves of Example 1 had an average cuff thickness of about 0.059 mm, an average palm thickness of about 0.115 mm, an average finger thickness of about 0.137 mm, an average weight of about 5.82 grams, and an average length of about 245 mm. The comparative purple nitrile gloves had an average cuff thickness of about 0.097 mm, an average palm thickness of about 0.122 mm, an average finger thickness of about 0.147 mm, an average weight of about 5.80 grams, and an average length of about 245 mm. Further, the gloves of Example 1 had an average modulus at 300% elongation of about 5.49 MPa, an average tensile strength of about 34.12 MPa, an average force at break of about 12.14 N, and an average percent elongation at break of about 672%, while the comparative purple nitrile gloves had an average modulus at 300% elongation of about 3.26 MPa, an average tensile strength of about 35.14 MPa, an average force at break of about 11.15 N, and an average percent elongation at break of about 666%. Further, the gloves included two separate colored layers (a blue grip side layer and a green donning side layer) so that the green of the donning side layer had a high level of contrast with the blue of the grip side layer for enhanced detection of any breaches of the blue grip side layer. In addition, the blue layer was uniformly colored and the green layer was uniformly colored, and the blue layer did not bleed into or muddy the green layer and vice versa.

Example 2

In Example 2, the ability to form a multilayered glove from a four-dip process having a black pigment grip side layer and an orange pigment donning side layer was demonstrated. A glove mold was first dipped in a first powder free coagulant containing 10 wt. % calcium nitrate. The mold was then dipped in a first nitrile rubber formulation containing 1 part of black pigment per 100 parts of nitrile rubber to form the grip side layer, where the grip side layer had a total solids content of 20%. Then, the mold was dipped in a second powder free coagulant containing 18 wt. % calcium nitrate. Thereafter, the mold was dipped in a second nitrile rubber formulation containing 10 parts titanium dioxide and 5 parts orange pigment per 100 parts of nitrile rubber to form the donning side layer, where the layer had a total solids content of 20%. The mold was dipped to the same level for both nitrile rubber formulations, then the cuff region of the glove was folded over after its removal from the mold to expose the lighter donning side layer at the cuff. Due at least in part to the second powder free coagulant layer having an increased concentration of calcium nitrate and lighter donning side layer having a sufficient amount of titanium dioxide filler, the grip side layer and donning side layer were maintained as separate layers, where the dark (black) grip side layer did not bleed through to the lighter (orange) donning side layer.

Example 3

In Example 3, the ability to form a multilayered glove from a three-dip process having a black pigment grip side layer and an orange pigment donning side layer was demonstrated. A glove mold was first dipped in a first powder free coagulant containing 18 wt. % calcium nitrate. The mold was then dipped in a first nitrile rubber formulation containing 1 part of black pigment per 100 parts of nitrile rubber to form the grip side layer, where the grip side layer had a total solids content of 20%. Thereafter, the mold was dipped in a second nitrile rubber formulation containing 10 parts titanium dioxide and 5 parts orange pigment per 100 parts of nitrile rubber to form the donning side layer, where the layer had a total solids content of 20%. The mold was dipped to the same level for both nitrile rubber formulations, then the cuff region of the glove was folded over after its removal from the mold to expose the lighter donning side layer at the cuff. Due at least in part to the lighter donning side layer having a sufficient amount of titanium dioxide filler, the grip side layer and donning side layer were maintained as separate layers, where the dark grip side layer did not bleed through to the lighter donning side layer.

Example 4

Figure 6:
FIG. 6 is a graph illustrating the mechanical properties of an unaged multilayered glove of the present invention as compared to a single layer nitrile glove and a single layer polyurethane glove.
Figure 7:
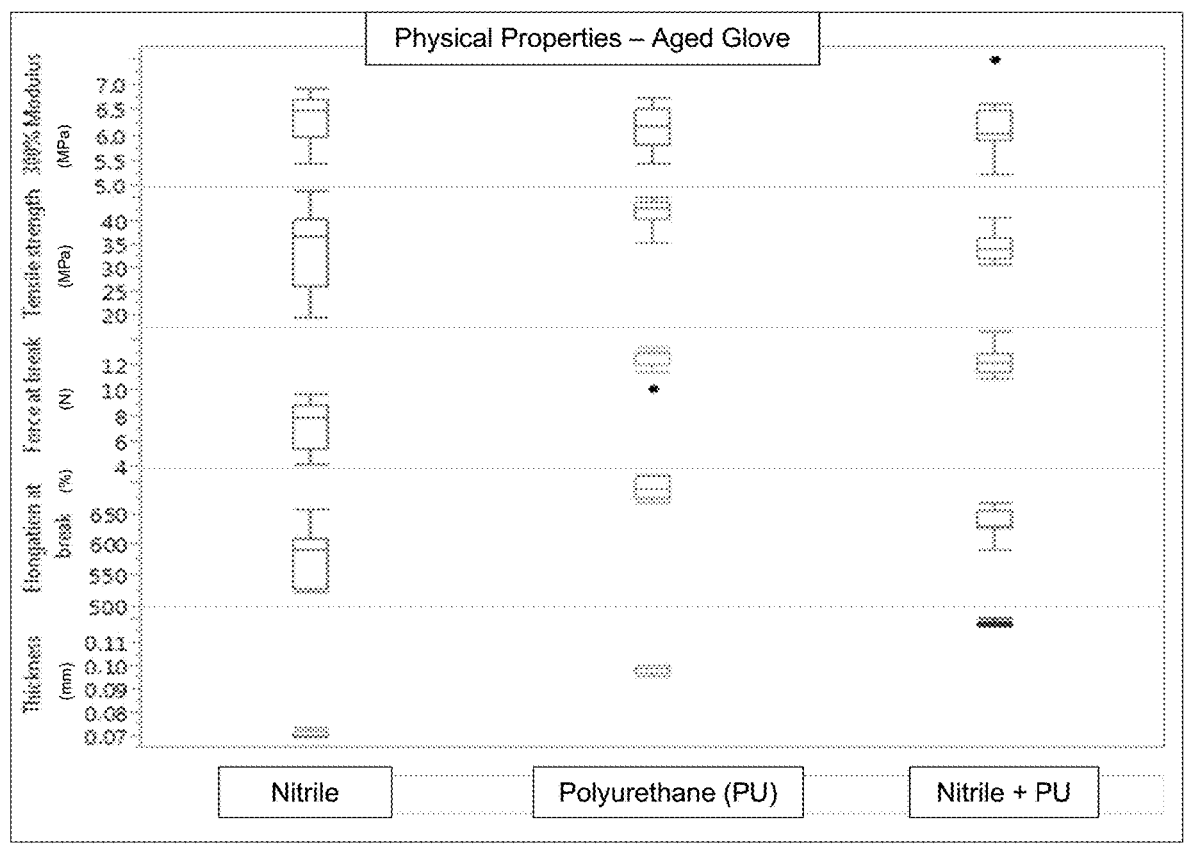
FIG. 7 is a graph illustrating the mechanical properties of an aged multilayered glove of the present invention as compared to a single layer nitrile glove and a single layer polyurethane glove.

Multilayered unaged and aged gloves formed as in Example 1 were subjected to mechanical testing and compared to a single layer nitrile rubber glove and a single layer polyurethane glove. The aged gloves were subjected to a temperature of 70° C. for 168 hours. The results are summarized in FIGS. 6 and 7. As shown, although the thickness of the polyurethane and nitrile rubber glove was increased compared to nitrile rubber alone or polyurethane alone, the glove thickness was still around 0.115 mm, where such a small thickness can provide for improved comfort and can also enhance tactile sensitivity to temperature and surface textures. In addition, despite having such a small thickness, the various colored layers of the nitrile rubber and polyurethane glove did not "bleed" through or show through other colored layers. Additionally, the multilayered aged and unaged nitrile rubber and polyurethane gloves of the present invention exhibited similar moduli at 300% elongation, tensile strength, and elongation at break as the convention nitrile rubber gloves, but exhibited an increased force at break compared to the conventional nitrile rubber gloves. Without intending to be limited by any particular theory, the increase in strength can be attributed to the addition of the polyurethane layer, which can provide increased glove resistance to tear, abrasion, and chemicals.

Example 5

In Example 5, various nitrile rubber formulations were compounded and utilized to compare the colorimetric properties between gloves formed via a 3-dip process (see FIG. 3) and gloves formed via a 4-dip process (see FIG. 4) contemplated by the present invention. Specifically, the formulations utilized to form the various layers of the gloves were black, orange, or white, where the resulting gloves included a grip side layer that was black, white, or orange, and a donning side layer that was black, white or orange. The formulations are shown in Tables 4-7 below, while the specific gloves formed are shown in Table 8.

TABLE 4

Black Layer

| Component | Parts Per 100 Parts of Nitrile Rubber |
| --- | --- |
| Nitrile Rubber | 100 |
| Potassium Hydroxide | 1.4 |
| Zinc Oxide | 1.35 |
| Sulfur | 1 |
| ZDEC | 0.25 |
| DPG | 0.5 |
| ZMBT | 0.25 |
| Black Pigment | 3 |
| Total Solids Content | 18% |

TABLE 5

Orange Layer

| Component | Parts Per 100 Parts of Nitrile Rubber |
| --- | --- |
| Nitrile Rubber | 100 |
| Potassium Hydroxide | 1.4 |
| Zinc Oxide | 1.35 |
| Sulfur | 1 |
| ZDEC | 0.25 |
| DPG | 0.5 |
| ZMBT | 0.25 |
| Titanium Dioxide | 10 |
| Farperse Orange | 10 |
| Farperse Red | 0.1 |
| Total Solids Content | 18% |

TABLE 6

White Layer 10 phr Titanium Dioxide

| Component | Parts Per 100 Parts of Nitrile Rubber |
| --- | --- |
| Nitrile Rubber | 100 |
| Potassium Hydroxide | 1.4 |
| Zinc Oxide | 1.35 |
| Sulfur | 1 |
| ZDEC | 0.25 |
| DPG | 0.5 |
| ZMBT | 0.25 |
| Titanium Dioxide | 10 |
| Total Solids Content | 18% |

TABLE 7

White Layer 3.5 phr Titanium Dioxide

| Component | Parts Per 100 Parts of Nitrile Rubber |
| --- | --- |
| Nitrile Rubber | 100 |
| Potassium Hydroxide | 1.4 |
| Zinc Oxide | 1.35 |
| Sulfur | 1 |
| ZDEC | 0.25 |
| DPG | 0.5 |
| ZMBT | 0.25 |
| Titanium Dioxide | 3.5 |
| Total Solids Content | 18% |

TABLE 8

Gloves Formed from Formulations in Table 4-Table 7

| Sample | Dip 1 - 1st Coagulant Dip (5 seconds) | Dip 2 - 1st Nitrile Rubber Formulation (Grip Side of Glove) (5 seconds) | Dip 3 - 2nd Coagulant Dip (5 seconds) | Dip 4 - 2nd Nitrile Rubber Formulation (Donning Side of Glove) (Samples 1-9: 8 seconds) (Samples 10-18: 3 seconds) |
|---|---|---|---|---|
| 1 | 12% calcium nitrate | White 3.5 phr TiO$_2$ | — | Black |
| 2 | 12% calcium nitrate | Black | — | White 3.5 phr TiO$_2$ |
| 3 | 12% calcium nitrate | Orange | — | Black |
| 4 | 12% calcium nitrate | Orange | — | White 3.5 phr TiO$_2$ |
| 5 | 12% calcium nitrate | White 3.5 phr TiO$_2$ | — | Orange |
| 6 | 12% calcium nitrate | White 10 phr TiO$_2$ | — | Black |
| 7 | 12% calcium nitrate | Black | — | White 10 phr TiO$_2$ |
| 8 | 12% calcium nitrate | Orange | — | White 10 phr TiO$_2$ |
| 9 | 12% calcium nitrate | White 10 phr TiO$_2$ | — | Orange |
| 10 | 12% calcium nitrate | White 3.5 phr TiO$_2$ | 5% calcium nitrate | Black |
| 11 | 12% calcium nitrate | Black | 5% calcium nitrate | White 3.5 phr TiO$_2$ |
| 12 | 12% calcium nitrate | Orange | 5% calcium nitrate | Black |
| 13 | 12% calcium nitrate | Orange | 5% calcium nitrate | White 3.5 phr TiO$_2$ |
| 14 | 12% calcium nitrate | White 3.5 phr TiO$_2$ | 5% calcium nitrate | Orange |
| 15 | 12% calcium nitrate | White 10 phr TiO$_2$ | 5% calcium nitrate | Black |
| 16 | 12% calcium nitrate | Black | 5% calcium nitrate | White 10 phr TiO$_2$ |
| 17 | 12% calcium nitrate | Orange | 5% calcium nitrate | White 10 phr TiO$_2$ |
| 18 | 12% calcium nitrate | White 10 phr TiO$_2$ | 5% calcium nitrate | Orange |

TABLE 9

Colorimetric L*a*b* Values of Table 6 Glove Samples

| | Grip Side of Glove | | | Donning Side of Glove | | |
|---|---|---|---|---|---|---|
| Sample | L* | a* | b* | L* | a* | b* |
| 1 | 69.0 | −1.9 | −3.2 | 13.0 | 1.9 | 18.0 |
| 2 | 16.7 | 0.9 | 13.3 | 56.3 | −1.9 | −4.1 |
| 3 | 59.7 | 40.8 | 66.7 | 14.7 | 3.5 | 19.4 |
| 4 | 63.2 | 51.7 | 73.1 | 72.6 | 34.0 | 26.7 |
| 5 | 78.7 | 22.5 | 14.8 | 63.9 | 50.7 | 77.8 |
| 6 | 85.2 | −1.5 | −2.3 | 11.8 | 1.9 | 19.3 |
| 7 | 18.9 | 0.7 | 10.9 | 78.3 | −1.7 | −3.2 |
| 8 | 62.9 | 53.1 | 77.3 | 82.1 | 17.5 | 11.2 |
| 9 | 88.0 | 8.7 | 6.2 | 64.0 | 52.4 | 78.7 |
| 10 | 67.7 | −1.8 | −3.7 | 12.7 | 1.9 | 17.2 |
| 11 | 18.1 | 1.1 | 11.8 | 57.8 | −1.9 | −4.5 |
| 12 | 59.9 | 39.4 | 69.6 | 11.4 | 1.9 | 19.7 |
| 13 | 63.2 | 51.9 | 73.3 | 74.5 | 30.1 | 22.4 |
| 14 | 77.4 | 25.1 | 14.2 | 63.7 | 51.2 | 79.1 |
| 15 | 84.1 | −1.3 | −2.7 | 12.0 | 1.4 | 18.8 |
| 16 | 17.8 | 1.0 | 11.9 | 77.4 | −1.8 | −3.4 |
| 17 | 63.4 | 52.1 | 75.5 | 84.0 | 14.6 | 8.3 |
| 18 | 87.2 | 9.9 | 6.2 | 64.4 | 51.4 | 73.8 |

As shown above in Table 9, the glove samples formed using a 4-dip process (samples 10-18) had generally the same color difference values as the samples formed using a 3-dip process (samples 1-9). However, the gloves formed using a 4-dip process can be made more efficiently because the 2nd coagulant dip (up to 5 seconds) and the 2nd rubber formulation dip (3 seconds) of the 4-dip process can require less time than the 2nd rubber formulation dip of the 3-dip process (8 seconds).

TABLE 10

Colorimetric L*a*b*c*h* Values of Various Glove Samples

| Description | L* | a* | b* | c* | h* |
|---|---|---|---|---|---|
| Comparative White/Black APEX Pro Glove, Black Grip Side | 26.3 | −1.0 | −4.9 | 5.0 | 258.2 |
| Black/Orange Glove, Black Grip Side | 20.8 | −0.2 | −0.4 | 0.5 | 244.5 |
| Black/Orange Glove, Orange Donning Side | 57.4 | 44.5 | 50.7 | 67.5 | 48.8 |
| Sample 6 from Table 9, Black Donning Side | 20.0 | −0.1 | −0.4 | −0.4 | 250.7 |
| Sample 15 from Table 9, Black Donning Side | 19.2 | 0.0 | −0.2 | 0.2 | 277.8 |

Note: For the black/orange glove in Table 10, the formulations in Tables 4 and 5 were used As shown above in Table 10, the orange donning side of the glove contemplated by the black side of the gloves of the present invention were closer to a pure black color (closer to an L* value of 0) compared to the black grip side of the APEX Pro comparative gloves. Moreover, the orange donning side of the gloves of the present invention had a high c* value of 67.5, which is indicative of a very high chroma (saturation) or color purity, resulting in a high level of contrast between the orange donning side of the glove and the black grip side of the glove, which enhances the breach detection capabilities of the glove.

Example 6

Next, in Example 6, the thickness at the finger area of the gloves of the present invention, formed using a 4-dip process, was compared to the thickness at the finger area of comparative commercially available gloves. The results are shown below in Table 11.

TABLE 11

Comparison of Glove Finger Thicknesses

| Glove Sample Grip/Donning sides | Grip Side Thickness (mm) | Donning Side Thickness (mm) | Total Thickness (mm) | Donning Side Thickness as % of Grip Side Thickness | Donning Side Thickness as % of Total Glove Thickness |
|---|---|---|---|---|---|
| Comparative White/Black APEX Pro Glove | 0.1237 | 0.0515 | 0.1752 | 41.6% | 29.4% |
| Comparative White/Blue Microflex Corporation Glove | 0.1357 | 0.0484 | 0.1841 | 35.7% | 26.3% |
| Black/Orange Glove from Table 10 | 0.0603 | 0.0382 | 0.0985 | 63.3% | 38.8% |

As shown in Table 11 above, gloves contemplated by the present invention (e.g., a black/orange glove) can be significantly thinner overall than commercially available gloves having two different colors on the grip and donning sides. Nevertheless, despite the gloves of the present invention being thinner, sufficient contrast still exists between the two layers so that breaches in the glove are more easily detected. Without intending to be limited by any particular theory, the present inventors have found that by forming a glove having a donning side layer that exhibits an increased total percentage of the overall thickness of the glove can contribute to the improved contrast and resulting improved breach detection capabilities of the gloves of the present invention. For instance, as shown above, the gloves contemplated by the present invention can have a donning side layer that is greater than about 30% of the overall thickness of the glove, such as from about 30% to about 90%, such as from about 32% to about 80%, such as from about 34% to about 60% of the overall thickness of the glove when measured at the finger region. In contrast, the donning side layer of the commercially available Microflex Corporation and APEX Pro gloves is less than 30% of the overall thickness of the glove when measured at the finger region.

The present invention has been described both in general and in detail by way of examples. These and other modifications and variations of the present invention may be practiced by those of ordinary skill in the art, without departing from the spirit and scope of the present invention. In addition, it should be understood that aspects of the various embodiments may be interchanged both in whole and in part. Furthermore, those of ordinary skill in the art will appreciate that the foregoing description is by way of example only, and is not intended to limit the invention so further described in such appended claims.

What is claimed is:

1. A multilayered elastomeric article comprising:
   a first layer, wherein the first layer includes a first elastomeric material compounded with a first colored pigment; and
   a second layer, wherein the second layer includes a second elastomeric material compounded with a second colored pigment and titanium dioxide, wherein the ratio of the parts of titanium dioxide to the parts of the second colored pigment ranges from about 0.25 to about 3, wherein a sufficient level of contrast exists between the first layer and the second layer to detect a breach of the first layer, wherein the first elastomeric material and the second elastomeric material each include nitrile rubber, wherein the nitrile rubber is compounded with an alkali agent, a metal oxide, a sulfur crosslinking agent, and a vulcanization accelerator.

2. The elastomeric article of claim 1, wherein the elastomeric article is a glove, further wherein the first layer defines a grip side layer of the glove and the second layer defines a donning side layer of the glove.

3. The elastomeric article of claim 2, where the glove includes a cuff, wherein the cuff is formed from the second layer.

4. The elastomeric article of claim 2, wherein the glove has a palm region thickness ranging from about 0.01 millimeters to about 6 millimeters.

5. The elastomeric article of claim 1, wherein the first layer is darker than the second layer, wherein the first layer and the second layer exhibit a ΔE* color difference greater than about 2.5 as determined according to the Commission Internationale de l'Eclairage (CIE) 1976 standard.

6. The elastomeric article of claim 1, wherein the second layer exhibits a saturation level of greater than about 25%.

7. The elastomeric article of claim 1, wherein the second layer exhibits a value level of greater than about 25%.

8. The elastomeric article of claim 1, wherein the first colored pigment is present in the first layer in an amount ranging from about 0.25 parts to about 5 parts based on 100 dry parts of the first elastomeric material.

9. The elastomeric article of claim 1, wherein the second colored pigment is present in the second layer in an amount ranging from about 0.5 parts to about 15 parts based on 100 dry parts of the second elastomeric material.

10. The elastomeric article of claim 9, wherein the titanium dioxide is present in the second layer in an amount ranging from about 0.25 parts to about 30 parts based on 100 dry parts of the second elastomeric material.

11. The elastomeric article of claim 1, wherein a mask is applied to form a graphic, pattern, logo, design, or text on the first layer, wherein the second layer is visible where the mask is applied.

12. The elastomeric article of claim 1, wherein a breach of the first layer exposes the second colored pigment of the second layer to facilitate detection of the breach.

13. The elastomeric article of claim 1, wherein the elastomeric article is reversible.

* * * * *